(12) United States Patent
Carr et al.

(10) Patent No.: US 12,128,168 B2
(45) Date of Patent: Oct. 29, 2024

(54) PRESSURE SAMPLING AND SUPPLY OF NEGATIVE PRESSURE IN NEGATIVE PRESSURE WOUND THERAPY

(71) Applicant: Smith & Nephew, Inc., Memphis, TN (US)

(72) Inventors: Raymond Carr, Tampa, FL (US); William W. Gregory, Gainesville, FL (US); Felix C. Quintanar, Hull (GB)

(73) Assignee: Smith & Nephew, Inc., Memphis, TN (US)

( * ) Notice: Subject to any disclaimer, the term of this patent is extended or adjusted under 35 U.S.C. 154(b) by 1125 days.

(21) Appl. No.: 16/784,699

(22) Filed: Feb. 7, 2020

(65) Prior Publication Data

US 2020/0171219 A1    Jun. 4, 2020

Related U.S. Application Data

(63) Continuation of application No. 15/540,979, filed as application No. PCT/US2015/061165 on Nov. 17, 2015, now Pat. No. 10,556,045.

(Continued)

(51) Int. Cl.
*A61M 1/00* (2006.01)

(52) U.S. Cl.
CPC .............. *A61M 1/73* (2021.05); *A61M 1/74* (2021.05); *A61M 1/96* (2021.05); *A61M 1/982* (2021.05);

(Continued)

(58) Field of Classification Search
CPC ............ A61M 1/73; A61M 1/74; A61M 1/96; A61M 1/982; A61M 2205/15;

(Continued)

(56) References Cited

U.S. PATENT DOCUMENTS

| 5,419,768 A | 5/1995 | Kayser |
| 5,449,347 A | 9/1995 | Preen et al. |

(Continued)

FOREIGN PATENT DOCUMENTS

| CA | 2819475 A1 | 6/2012 |
| CA | 2851495 A1 | 4/2013 |

(Continued)

OTHER PUBLICATIONS

International Preliminary Report on Patentability for Application No. PCT/US2015/061165, mailed on Jul. 13, 2017, 7 pages.

(Continued)

*Primary Examiner* — Benjamin J Klein

(74) *Attorney, Agent, or Firm* — Knobbe, Martens, Olson & Bear, LLP

(57) ABSTRACT

Embodiments of negative pressure wound therapy systems and methods for operating the systems are disclosed. In some embodiments, a system includes a pump assembly, canister, and a wound dressing configured to be positioned over a wound. The pump assembly, canister, and wound dressing can be fluidically connected to facilitate delivery of negative pressure to the wound. The system can be configured to deliver negative pressure based at least on a sensed pressured in a fluid flow path connecting a pump of the pump assembly and the wound dressing. The sensed pressure can be sampled, in some embodiments, synchronous with operation of the pump and can be used for controlling (Continued)

the pump. Increased efficiency, diminished noise and vibration caused by operation of the pump, reduced in energy usage, and better comfort for the patient can be attained.

22 Claims, 14 Drawing Sheets

Related U.S. Application Data

(60) Provisional application No. 62/097,765, filed on Dec. 30, 2014.

(52) U.S. Cl.
CPC ..... *A61M 2205/15* (2013.01); *A61M 2205/18* (2013.01); *A61M 2205/3337* (2013.01); *A61M 2205/3341* (2013.01); *A61M 2205/3344* (2013.01); *A61M 2205/3365* (2013.01); *A61M 2205/50* (2013.01); *A61M 2205/502* (2013.01); *A61M 2205/581* (2013.01); *A61M 2205/587* (2013.01); *A61M 2205/702* (2013.01); *A61M 2205/8206* (2013.01); *A61M 2209/084* (2013.01)

(58) Field of Classification Search
CPC ...... A61M 2205/18; A61M 2205/3337; A61M 2205/3344; A61M 2205/3365; A61M 2205/50; A61M 2205/502; A61M 2205/581; A61M 2205/587; A61M 2205/702; A61M 2205/8206; A61M 2209/084
See application file for complete search history.

(56) References Cited

U.S. PATENT DOCUMENTS

| | | | |
|---|---|---|---|
| 5,622,429 | A | 4/1997 | Heinze |
| 6,241,739 | B1 | 6/2001 | Waldron |
| 6,572,530 | B1 | 6/2003 | Araki et al. |
| 6,605,032 | B2 | 8/2003 | Benkowski et al. |
| 7,004,915 | B2 | 2/2006 | Boynton et al. |
| 7,022,113 | B2 | 4/2006 | Lockwood et al. |
| 7,361,184 | B2 | 4/2008 | Joshi |
| 7,503,910 | B2 | 3/2009 | Adahan |
| 7,553,306 | B1 | 6/2009 | Hunt et al. |
| 7,612,247 | B2 | 11/2009 | Oyaski |
| 7,670,323 | B2 | 3/2010 | Hunt et al. |
| 7,678,090 | B2 | 3/2010 | Risk et al. |
| 7,708,724 | B2 | 5/2010 | Weston |
| 7,723,560 | B2 | 5/2010 | Lockwood et al. |
| 7,763,000 | B2 | 7/2010 | Risk et al. |
| 7,776,028 | B2 | 8/2010 | Miller et al. |
| 7,811,269 | B2 | 10/2010 | Boynton et al. |
| 7,846,141 | B2 | 12/2010 | Weston |
| 7,857,806 | B2 | 12/2010 | Karpowicz et al. |
| 7,927,319 | B2 | 4/2011 | Lawhorn |
| 8,062,272 | B2 | 11/2011 | Weston |
| 8,105,295 | B2 | 1/2012 | Blott et al. |
| 8,167,869 | B2 | 5/2012 | Wudyka |
| 8,282,611 | B2 | 10/2012 | Weston |
| 8,294,586 | B2 | 10/2012 | Pidgeon et al. |
| 8,308,714 | B2 | 11/2012 | Weston et al. |
| 8,323,264 | B2 | 12/2012 | Weston et al. |
| 8,353,857 | B2 | 1/2013 | Rosenberg |
| 8,366,692 | B2 | 2/2013 | Weston et al. |
| 8,377,016 | B2 | 2/2013 | Argenta et al. |
| 8,444,392 | B2 | 5/2013 | Turner et al. |
| 8,494,349 | B2 | 7/2013 | Gordon |
| 8,535,296 | B2 | 9/2013 | Blott et al. |
| 8,540,688 | B2 | 9/2013 | Eckstein et al. |
| 8,617,129 | B2 | 12/2013 | Hartwell |
| 8,663,200 | B2 | 3/2014 | Weston et al. |
| 8,668,677 | B2 | 3/2014 | Eckstein et al. |
| 8,694,600 | B2 | 4/2014 | Gaines et al. |
| 8,734,425 | B2 | 5/2014 | Nicolini |
| 8,785,059 | B2 | 7/2014 | Hartwell |
| 8,791,316 | B2 | 7/2014 | Greener |
| 8,814,841 | B2 | 8/2014 | Hartwell |
| 8,814,842 | B2 | 8/2014 | Coulthard et al. |
| 8,834,451 | B2 | 9/2014 | Blott et al. |
| 8,843,327 | B2 | 9/2014 | Vernon-Harcourt et al. |
| 8,845,603 | B2 | 9/2014 | Middleton et al. |
| 8,852,149 | B2 | 10/2014 | Weston et al. |
| 8,852,170 | B2 | 10/2014 | Weston et al. |
| 8,905,985 | B2 | 12/2014 | Allen et al. |
| 8,945,074 | B2 | 2/2015 | Buan et al. |
| 8,951,235 | B2 | 2/2015 | Allen et al. |
| 8,974,429 | B2 | 3/2015 | Gordon et al. |
| 9,017,286 | B2 | 4/2015 | Kamen et al. |
| 9,019,681 | B2 | 4/2015 | Locke et al. |
| 9,067,003 | B2 | 6/2015 | Buan et al. |
| 9,084,845 | B2 | 7/2015 | Adie et al. |
| 9,138,517 | B2 | 9/2015 | Garrigue |
| 9,180,231 | B2 | 11/2015 | Greener |
| 9,220,822 | B2 | 12/2015 | Hartwell |
| 9,227,000 | B2 | 1/2016 | Fink et al. |
| 9,408,954 | B2 | 8/2016 | Gordon et al. |
| 9,427,505 | B2 | 8/2016 | Askem et al. |
| 9,452,244 | B2 | 9/2016 | Blott et al. |
| 9,526,817 | B2 | 12/2016 | Blott et al. |
| 9,642,950 | B2 | 5/2017 | Hartwell |
| 9,757,501 | B2 | 9/2017 | Jennings et al. |
| 2001/0013822 | A1 | 8/2001 | Nazarian et al. |
| 2001/0031944 | A1 | 10/2001 | Peterson et al. |
| 2001/0049609 | A1 | 12/2001 | Girouard et al. |
| 2002/0082568 | A1 | 6/2002 | Yam |
| 2002/0161317 | A1 | 10/2002 | Risk et al. |
| 2002/0193679 | A1 | 12/2002 | Malave et al. |
| 2003/0028175 | A1 | 2/2003 | D'Antonio |
| 2004/0039255 | A1 | 2/2004 | Simonsen et al. |
| 2004/0059284 | A1 | 3/2004 | Nash et al. |
| 2004/0064132 | A1 | 4/2004 | Boehringer et al. |
| 2004/0171982 | A1 | 9/2004 | Danchin |
| 2004/0181314 | A1 | 9/2004 | Zaleski |
| 2005/0065471 | A1 | 3/2005 | Kuntz |
| 2005/0256447 | A1 | 11/2005 | Richardson et al. |
| 2005/0261805 | A1 | 11/2005 | Mori et al. |
| 2006/0029675 | A1 | 2/2006 | Ginther |
| 2006/0129137 | A1 | 6/2006 | Lockwood et al. |
| 2006/0229557 | A1 | 10/2006 | Fathallah et al. |
| 2007/0005029 | A1 | 1/2007 | Hopkins et al. |
| 2007/0016152 | A1 | 1/2007 | Karpowicz et al. |
| 2007/0032762 | A1 | 2/2007 | Vogel |
| 2007/0032763 | A1 | 2/2007 | Vogel |
| 2007/0118096 | A1 | 5/2007 | Smith et al. |
| 2007/0179460 | A1 | 8/2007 | Adahan |
| 2007/0219480 | A1 | 9/2007 | Kamen et al. |
| 2008/0005000 | A1 | 1/2008 | Radl et al. |
| 2008/0041401 | A1 | 2/2008 | Casola et al. |
| 2008/0071209 | A1 | 3/2008 | Moubayed et al. |
| 2008/0077091 | A1 | 3/2008 | Mulligan |
| 2008/0091175 | A1 | 4/2008 | Frikart et al. |
| 2008/0177224 | A1 | 7/2008 | Kelly et al. |
| 2008/0234641 | A1 | 9/2008 | Locke et al. |
| 2009/0030402 | A1 | 1/2009 | Adahan |
| 2009/0037216 | A1 | 2/2009 | Bluemler et al. |
| 2009/0043268 | A1 | 2/2009 | Eddy et al. |
| 2009/0099867 | A1 | 4/2009 | Newman |
| 2009/0105670 | A1 | 4/2009 | Bentley et al. |
| 2009/0182266 | A1 | 7/2009 | Gordon et al. |
| 2009/0206017 | A1 | 8/2009 | Rohde et al. |
| 2009/0299306 | A1 | 12/2009 | Buan |
| 2010/0022990 | A1 | 1/2010 | Karpowicz et al. |
| 2010/0036333 | A1 | 2/2010 | Schenk, III et al. |
| 2010/0042074 | A1 | 2/2010 | Weston et al. |
| 2010/0069829 | A1 | 3/2010 | Hutchinson et al. |
| 2010/0114026 | A1 | 5/2010 | Karratt et al. |
| 2010/0259406 | A1 | 10/2010 | Caso et al. |
| 2010/0305490 | A1 | 12/2010 | Coulthard et al. |
| 2011/0009824 | A1 | 1/2011 | Yodfat et al. |
| 2011/0015587 | A1 | 1/2011 | Tumey et al. |
| 2011/0015593 | A1 | 1/2011 | Svedman et al. |

(56) References Cited

U.S. PATENT DOCUMENTS

| | | |
|---|---|---|
| 2011/0028881 A1 | 2/2011 | Basaglia |
| 2011/0028882 A1 | 2/2011 | Basaglia |
| 2011/0034861 A1 | 2/2011 | Schaefer |
| 2011/0040288 A1 | 2/2011 | Eckstein et al. |
| 2011/0063117 A1 | 3/2011 | Turner et al. |
| 2011/0077605 A1* | 3/2011 | Karpowicz ............ A61M 1/982 604/319 |
| 2011/0092958 A1 | 4/2011 | Jacobs |
| 2012/0001762 A1 | 1/2012 | Turner et al. |
| 2012/0035560 A1 | 2/2012 | Eddy et al. |
| 2012/0046625 A1 | 2/2012 | Johannison |
| 2012/0157941 A1 | 6/2012 | Luckemeyer et al. |
| 2012/0197196 A1 | 8/2012 | Halbert et al. |
| 2012/0271256 A1 | 10/2012 | Locke et al. |
| 2012/0289914 A1 | 11/2012 | Eckstein et al. |
| 2013/0023719 A1 | 1/2013 | Bennett |
| 2013/0062265 A1 | 3/2013 | Balschat et al. |
| 2013/0144227 A1 | 6/2013 | Locke et al. |
| 2013/0165821 A1 | 6/2013 | Freedman et al. |
| 2013/0267919 A1 | 10/2013 | Caso et al. |
| 2013/0296816 A1 | 11/2013 | Greener |
| 2013/0303975 A1 | 11/2013 | Gvodas, Jr. |
| 2013/0310781 A1 | 11/2013 | Phillips et al. |
| 2013/0317463 A1 | 11/2013 | Yao et al. |
| 2013/0327326 A1 | 12/2013 | Brennan |
| 2014/0058344 A1 | 2/2014 | Toth |
| 2015/0025482 A1 | 1/2015 | Begin et al. |
| 2015/0051560 A1 | 2/2015 | Askem |
| 2015/0159066 A1 | 6/2015 | Hartwell et al. |
| 2015/0174304 A1 | 6/2015 | Askem et al. |
| 2015/0261920 A1 | 9/2015 | Blick |
| 2015/0269323 A1 | 9/2015 | Ginsburg |
| 2016/0136339 A1 | 5/2016 | Begin et al. |
| 2016/0184496 A1 | 6/2016 | Jaecklein et al. |
| 2017/0004106 A1 | 1/2017 | Joshua et al. |
| 2017/0007748 A1 | 1/2017 | Locke et al. |
| 2017/0368239 A1 | 12/2017 | Askem et al. |

FOREIGN PATENT DOCUMENTS

| | | |
|---|---|---|
| EP | 1684146 A2 | 7/2006 |
| EP | 2366721 A1 | 9/2011 |
| EP | 2066365 B1 | 4/2015 |
| GB | 2235877 A | 3/1991 |
| WO | WO 01/14048 A1 | 3/2001 |
| WO | WO 03/101508 A2 | 12/2003 |
| WO | WO 2008/036360 A2 | 3/2008 |
| WO | WO 2008/039314 A2 | 4/2008 |
| WO | WO 2008/049029 A2 | 4/2008 |
| WO | WO 2009/047524 A2 | 4/2009 |
| WO | WO 2009/093116 A1 | 7/2009 |
| WO | WO 2009/151645 A2 | 12/2009 |
| WO | WO 2010/039481 A1 | 4/2010 |
| WO | WO 2010/145780 A1 | 12/2010 |
| WO | WO 2011/023275 A1 | 3/2011 |
| WO | WO 2012/027342 A1 | 3/2012 |
| WO | WO 2012/027914 A1 | 3/2012 |
| WO | WO 2012/027915 A1 | 3/2012 |
| WO | WO 2012/100624 A1 | 8/2012 |
| WO | WO 2013/014278 A1 | 1/2013 |
| WO | WO 2014/151930 A2 | 9/2014 |
| WO | WO 2016/109041 A1 | 7/2016 |

OTHER PUBLICATIONS

International Search Report and Written Opinion for Application No. PCT/US2014/050233, mailed on Jan. 7, 2015, 16 pages.
International Search Report and Written Opinion for Application No. PCT/US2015/061165, mailed on Feb. 25, 2016, 8 pages.
"Synchronous", Merriam-Webster, accessed on Nov. 5, 2019 from https://www.merriam-webster.com/dictionary/synchronous, 8 pages.

* cited by examiner

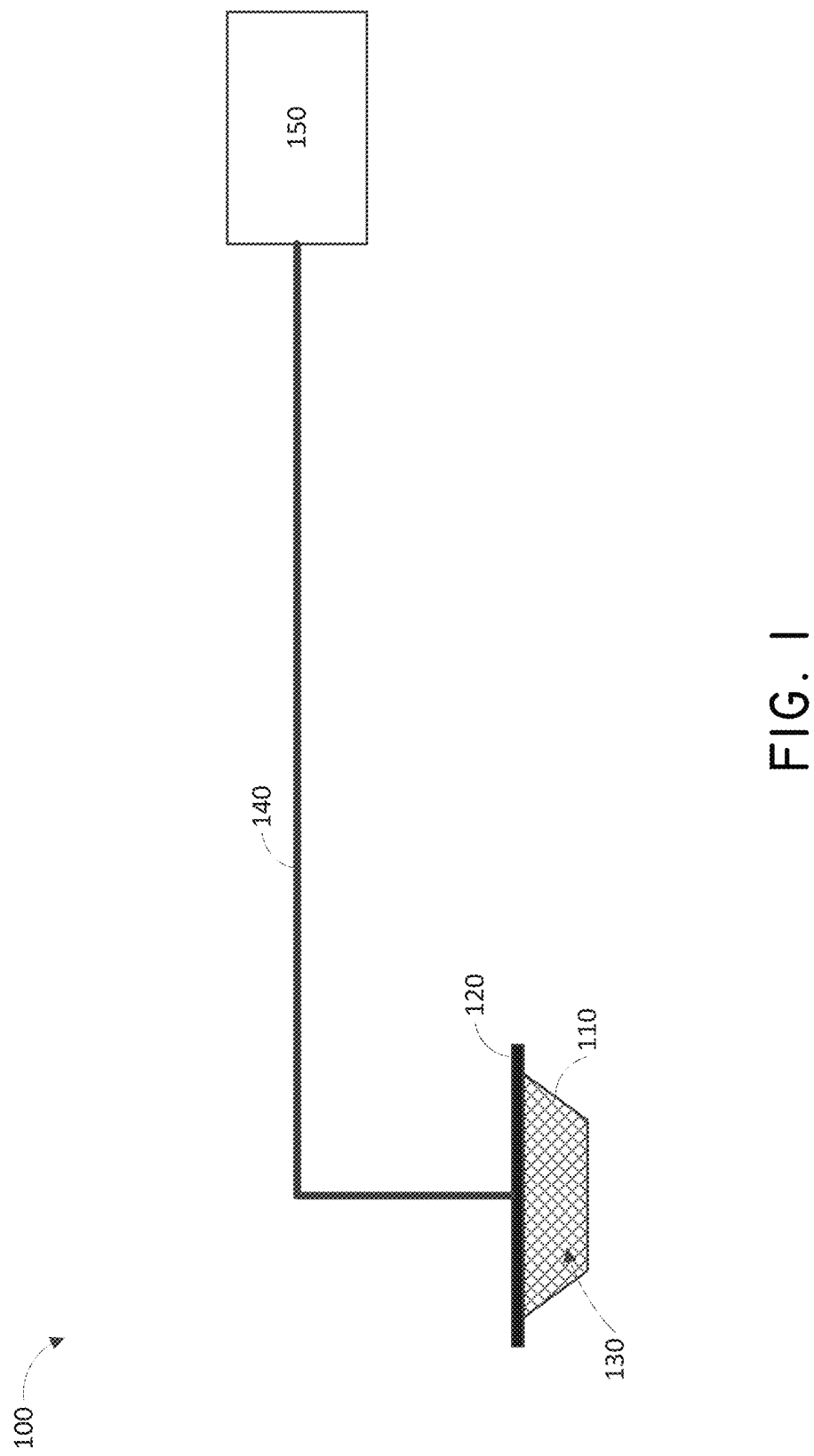

PRESSURE SAMPLING AND SUPPLY OF NEGATIVE PRESSURE IN NEGATIVE PRESSURE WOUND THERAPY

CROSS-REFERENCE TO RELATED APPLICATIONS

This application is a continuation of U.S. patent application Ser. No. 15/540,979, filed Jun. 29, 2017, which is a national stage application of International Patent Application No. PCT/US2015/061165, filed Nov. 17, 2015, which claims the benefit of U.S. Provisional Application No. 62/097,765, filed Dec. 30, 2014; the disclosures of which are hereby incorporated by reference in their entireties.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

In some embodiments, an apparatus for applying negative pressure therapy to a wound includes a housing, a pressure sensor, and a controller. The housing can include a source of negative pressure in fluidic communication with a wound dressing. The source of negative pressure can include a motor configured to operate one or more valves to open and close to aspirate fluid from the wound. The pressure sensor can measure pressure in a fluid flow path that fluidically connects the wound dressing and the source of negative pressure. The controller can operate the source of negative pressure (for example, the motor) using a drive signal. In addition, the controller can receive measurements of pressure in the fluid flow path from the pressure sensor, cause sampling or sample the measurements synchronous with opening and/or closing of at least one valve of the one or more valves, determine an estimated pressure level in the fluid flow path based at least on the sampled measurements, and generate the drive signal based at least on the estimated pressure level.

In some embodiments, an apparatus for applying negative pressure therapy to a wound includes a housing, a pressure sensor, and a controller. The housing can include a source of negative pressure configured to be in fluidic communication with a wound dressing. The source of negative pressure can include at least one valve. The pressure sensor can measure pressure in a fluid flow path configured to fluidically connect the wound dressing and the source of negative pressure. The controller can operate the source of negative pressure using a drive signal. In addition, the controller can determine a pressure measurement based on the pressure measured by the pressure sensor and generate the drive signal based at least on the determined pressure. The controller can perform the pressure measurement determination synchronous with operation of the source of negative pressure.

The apparatus of the preceding paragraph can include one or more of the following features: The controller can determine the pressure synchronous with opening and/or closing of the at least one valve. The pressure measured by the pressure sensor can include one or more components due to a pressure transient generated by the opening and/or closing of the at least one valve, and the one or more of the components can be substantially excluded from the determination of the pressure measurement. The pressure transient can be periodically generated by the at least one valve. The controller can determine the pressure measurement synchronous with the opening and/or closing of the at least one valve by sampling the measurements at a frequency that exceeds the frequency with which the at least one valve opens and/or closes. The sample frequency can be proportional to the frequency with which the at least one valve opens and/or closes. The controller can determine the pressure measurement synchronous with operation of the source of negative pressure based on one or more of the measurements obtained at times when the at least one valve may be in a first position and not based on one or more of the measurements obtained at times when the at least one valve may be in a second position. The source of negative pressure can include a vacuum pump having a motor, and the controller can determine the pressure measurement synchronous with the operation of the source of negative pressure based at least on a speed of the motor. The apparatus can further include a tachometer configured to measure the speed of the motor and generate a signal indicative of the measured speed of the motor, and the controller can determine the pressure measurement synchronous with the operation of the source of negative pressure based on the signal received from the tachometer. The controller can determine the pressure measurement synchronous with the operation of the source of negative pressure in response to a rising edge of the speed signal and in response to a falling edge of the speed signal. The controller can determine the pressure measurement synchronous with the operation of the source of negative pressure based on a signal received from the source of negative pressure. The at least one valve can include an inlet valve and an outlet valve. The controller can determine the pressure measurement synchronous with the operation of the source of negative pressure by applying a low-pass filter a plurality of measurements obtained from the pressure sensor. The controller can determine the pressure measurement asynchronous with the operation of the source of negative pressure in response to determining that an activity of the source of negative pressure falls below an activity threshold. The controller can control the source of negative pressure using pulse-width modulation (PWM) and generate the drive signal using a proportional-integral-derivative (PID) calculation based at least on a difference between a pressure setpoint and the determined pressure. The controller can generate the drive signal to have a 0% duty cycle in response to determining that the determined pressure exceeds a first threshold. The controller can generate the drive signal to have a 100% duty cycle in response to determining that a proportional term of the PID calculation exceeds a first threshold. The controller can generate the drive signal to have a 100% duty cycle in response to determining that a sum of a proportional term of the PID calculation and an integral term of the PID calculation exceeds a first threshold. The controller can set an integral term of the PID calculation to be 0 and an accumulated error of the PID calculation to be 0 in response to determining that the accumulated error is less than 0. The controller can set an accumulated error of the PID calculation to be greater than a sum of the accumulated error and the difference in response to determining that the difference is negative. The controller can determine the pressure measurement by sampling the pressure measured by the pressure sensor.

A method of operating the apparatus of any of the preceding three paragraphs can be performed.

BRIEF DESCRIPTION OF THE DRAWINGS

Embodiments of the present disclosure will now be described hereinafter, by way of example only, with reference to the accompanying drawings in which:

FIG. 1 illustrates a reduced pressure wound therapy system according to some embodiments.

DETAILED DESCRIPTION OF SOME EMBODIMENTS

Overview

Figure 2A:
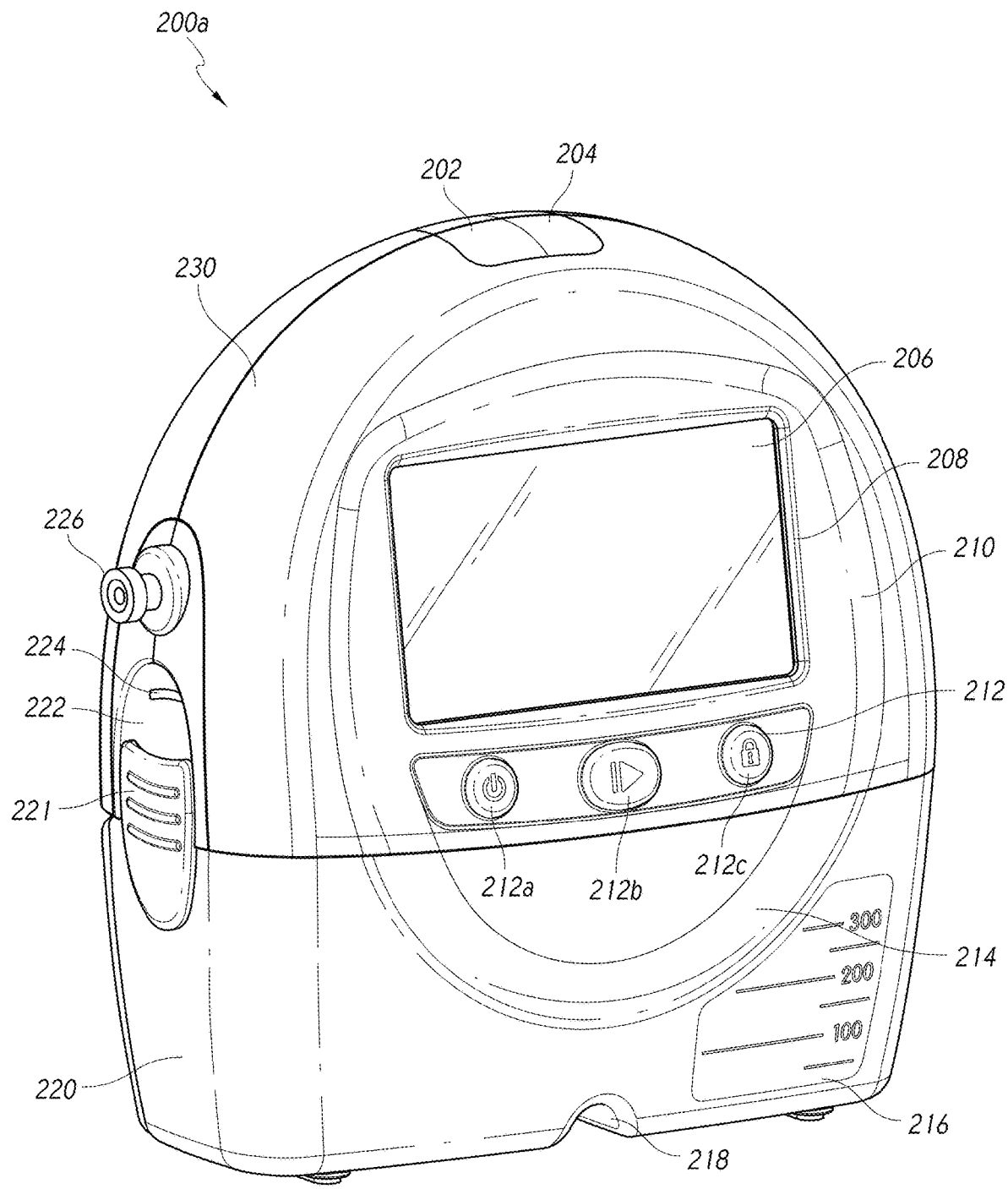
FIGS. 2A-2C illustrate a pump assembly and canister according to some embodiments.

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and conduit 140 so that the conduit 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

FIG. 2A illustrates a front view 200A of a pump assembly 230, such as the pump assembly 150, and canister 220 according to some embodiments. As is illustrated, the pump assembly 230 and the canister 220 are connected, thereby forming a device. The pump assembly 230 comprises one or more indicators, such as visual indicator 202 configured to indicate alarms and visual indicator 204 configured to indicate status of the TNP system. The indicators 202 and 204 can be configured to alert a user, such as patient or medical care provider, to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw a user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 comprises one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 and/or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted and/or various additional features are added to the canister 220. Any of the disclosed canisters may include or may omit a solidifier.

Figure 2B:
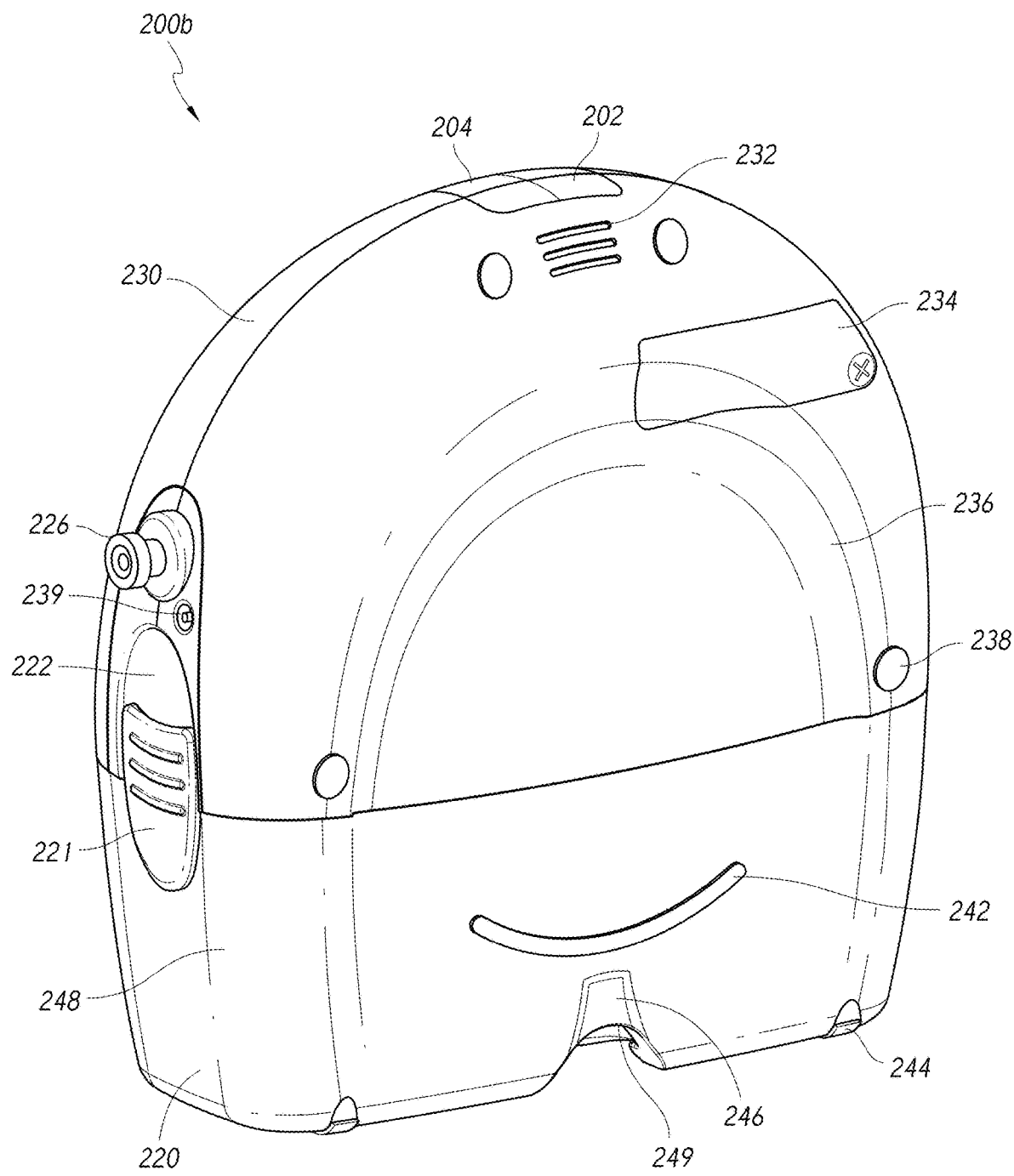

FIG. 2B illustrates a rear view 200B of the pump assembly 230 and canister 220 according to some embodiments. The pump assembly 230 comprises a speaker port 232 for producing sound. The pump assembly 230 includes a filter access door 234 for accessing and replacing one or more filters, such as antibacterial filters. The pump assembly 230 comprises a gripping portion 236 formed in the case of the pump assembly 230. The gripping portion 236 can be configured to allow the user to hold the pump assembly 230, such as during removal of the canister 220. The pump assembly 230 includes one or more covers 238 configured to as screw covers and/or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly 230 can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
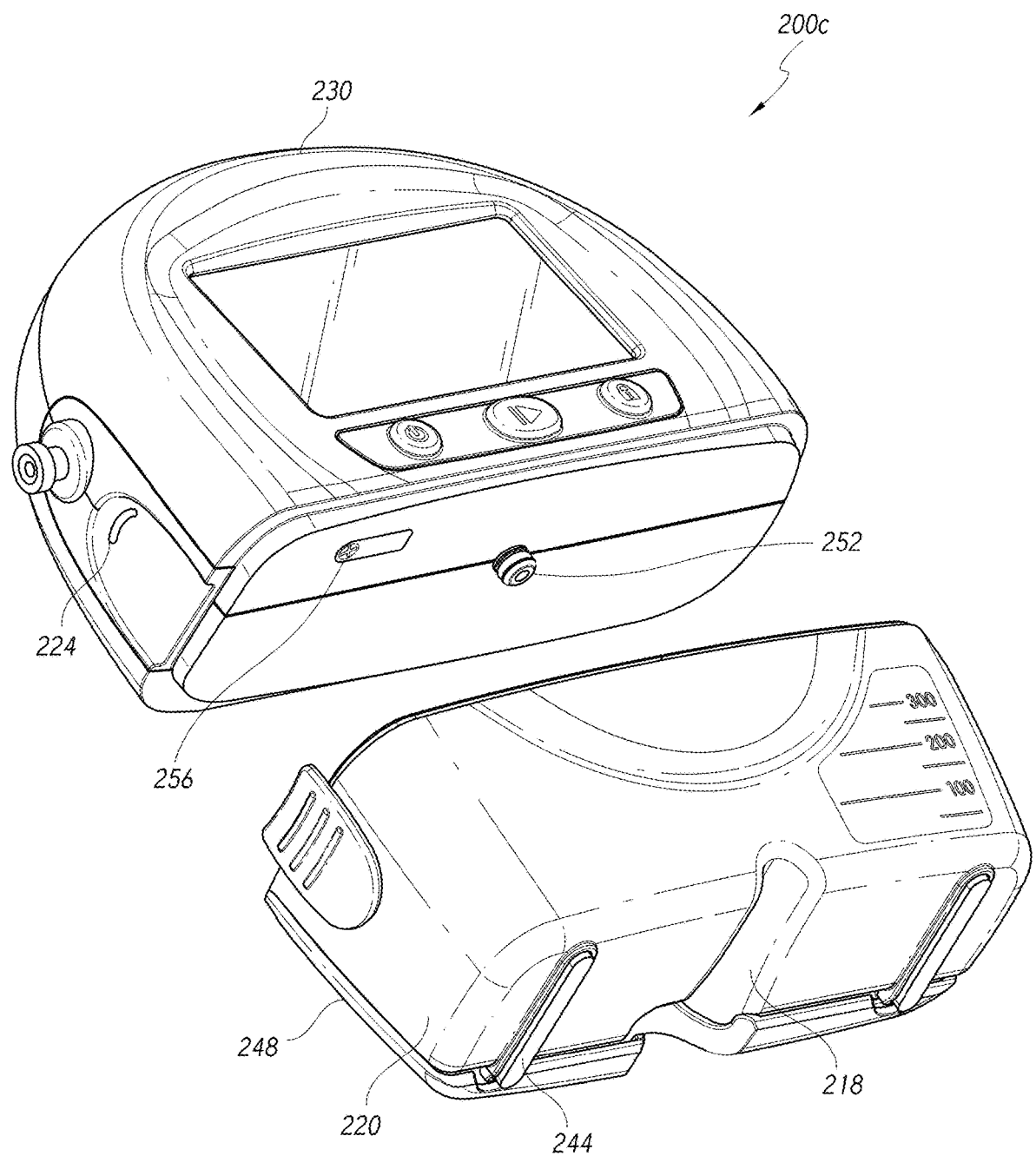

FIG. 2C illustrates a view 200C of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, and/or hybrid data transfer interfaces, such as SD, Compact Disc (CD), DVD, FireWire, Thunderbolt, PCI Express, and the like. In other embodiments, one or more of these additional ports are accessed through the door 234.

Additional description of the pump assembly 230 is disclosed in U.S. patent application Ser. No. 14/210,062, filed on Mar. 13, 2014 and titled "SYSTEMS AND METHODS FOR APPLYING REDUCED PRESSURE THERAPY," which is incorporated by reference in its entirety.

Electronics and Software

Figure 3:
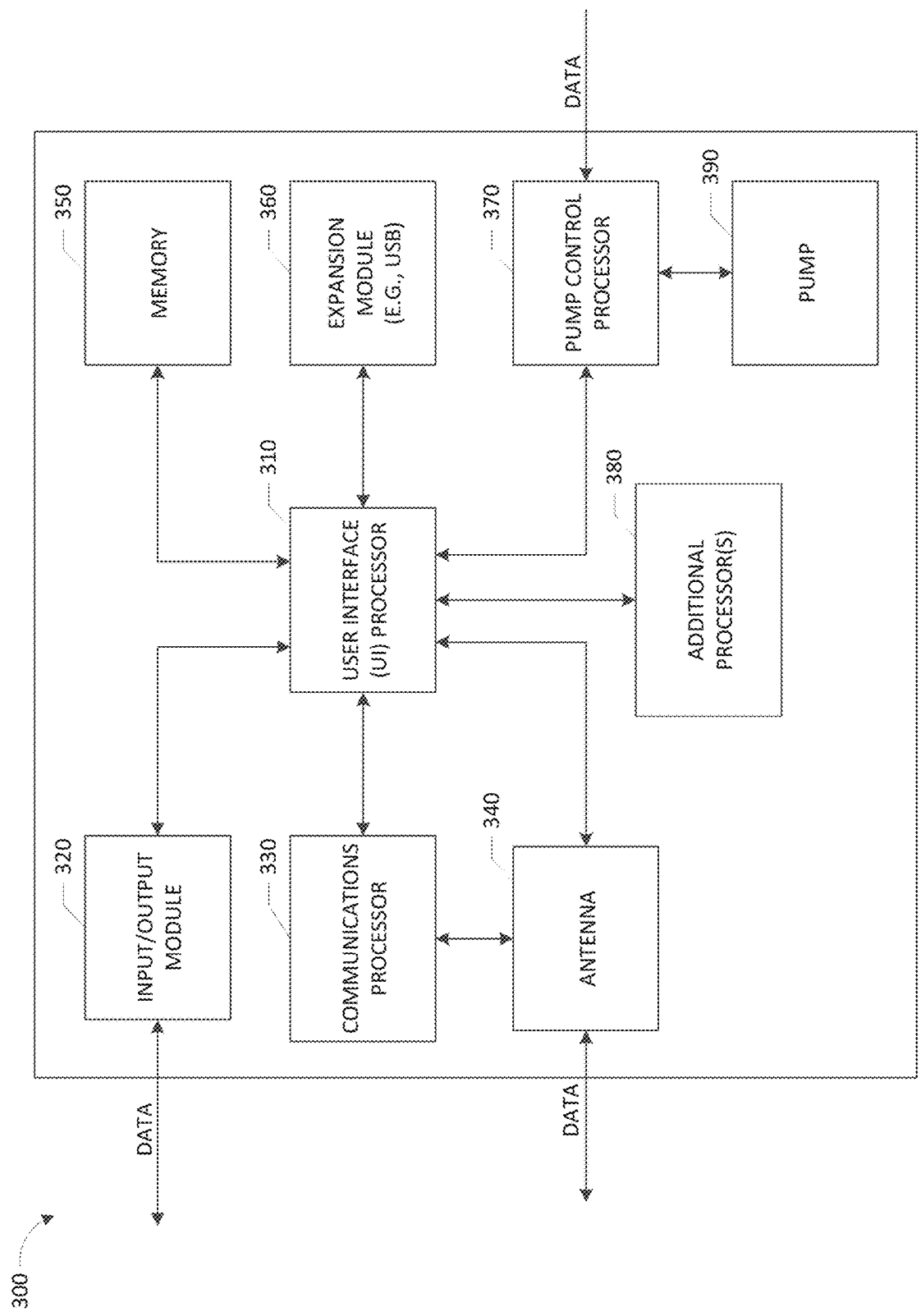
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can comprise a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump can include one or more valves, such as inlet and outlet (or exhaust) valves. The valves can be configured to open and close to enable the pump to aspirate fluid from the wound cavity 110. The pump control processor 370 can measure pressure in a fluid flow path, using data received from one or more pressure sensors, calculate the rate of fluid flow, and control the pump. The pump control processor 370 can control a pump motor so that a desired level of negative pressure is achieved in the wound cavity 110. The desired level of negative pressure can be pressure set or selected by the user. In various embodiments, the pump control processor 370 controls the pump (e.g., pump motor) using pulse-width modulation (PWM). A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory and/or can utilize memory 350. The pump control processor 370 can be a low-power processor. In some embodiments, processor 310 is configured to control the pump 390, and pump control processor 370 is not used.

A communications processor 330 can be configured to provide wired and/or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory and/or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, and/or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

Figure 4:
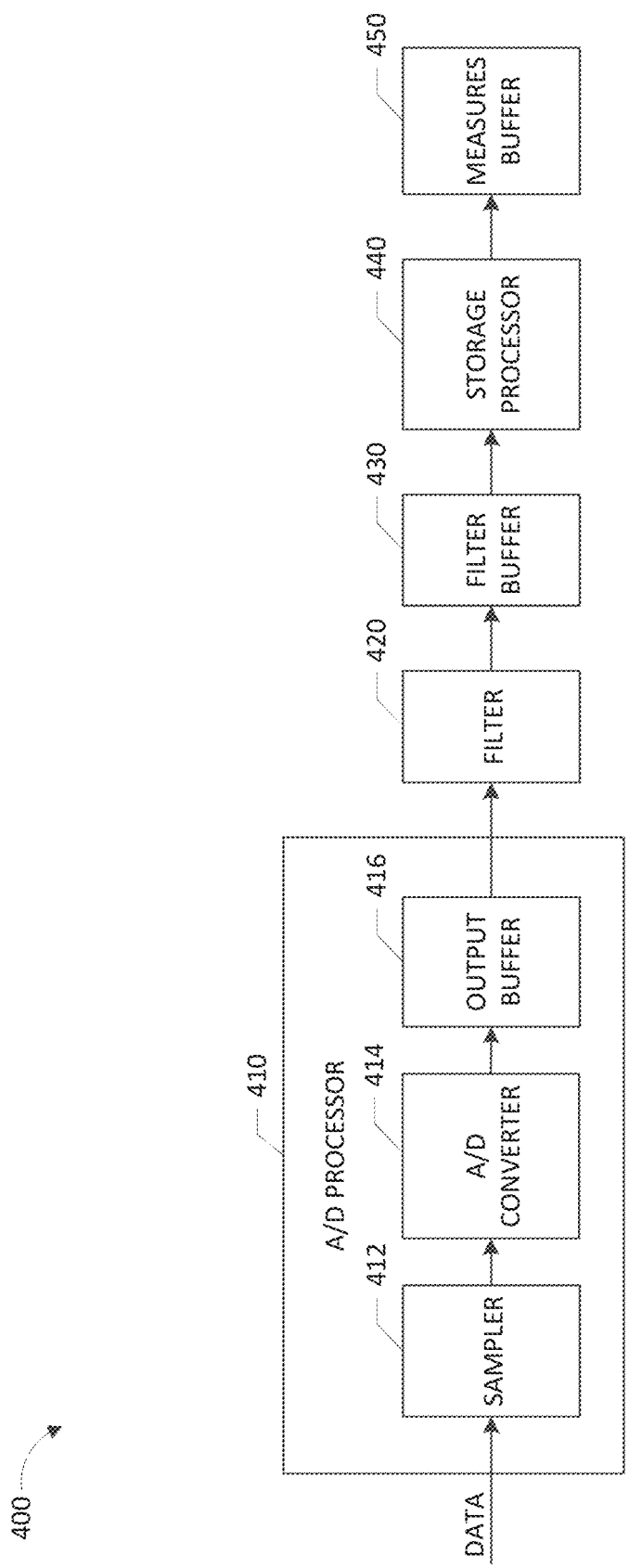
FIG. 4 illustrates an electrical component schematic of components of a pump control processor according to some embodiments.

Controlling the Operation of a Negative Pressure Source Using Synchronous Sampling FIG. 4 illustrates an electrical component schematic 400 of example components of a pump control processor, such as the pump control processor 370, according to some embodiments. Although the components can be part of the pump control processor, one or more of the components may be separate from the pump control processor in other embodiments. The components of the pump control processor can be used to sample a pressure signal provided by a pressure sensor of a pump assembly, such as the pump assembly 230. The pressure sensor can sense the pressure in or near an inlet, such as the inlet 252, (or canister connection) of the pump assembly to generate the pressure signal. This pressure sensor can measure the pressure in the canister (or in or near the dressing in a canisterless system). Moreover, although the components may be described in the context of sampling of a pressure signal, one or more other signals (e.g., motor voltage or current signals) can be sampled similarly or in accordance with a similar or the same timing using the components in other embodiments.

In some embodiments, opening (or closing) of the inlet valve causes a pressure transient in the fluid flow path. Opening (or closing) of the outlet valve can also cause transmission of the pressure transient. Measuring pressure values in the presence of the transient and using the measured pressure values to control the pump may cause inaccuracies and errors. Accordingly, it can be advantageous to synchronize the pressure measurements (and pump control) to durations when the pressure transient is not present in the fluid flow path. In certain embodiments, pressure measurements of the pressure sensor are read (for example, sampled) so as to be synchronized to "miss" the pressure transients caused by operation of the pump, such as due to the closing and/or opening of the at least one valve. This can be referred to as "synchronous" sampling. By contrast, reading pressure sensor measurements without regard to the operation of the pump (for example, opening and/or closing of the valves) can be referred to as "asynchronous" sampling. Whether sampling is synchronous or asynchronous, measured pressure can be used for controlling the pump as explained below.

In some embodiments, synchronous sampling can be performed as follows. The pressure sensor can provide the pressure signal to a sampler module or sampler 412 of an analog/digital (A/D) processor 410. The sampler can be a sample and hold device. The sampler 412 can sample the pressure signal with a frequency, such as 500 Hz, 1 kHz, 2 KHz, or 10 KHz, so that the sampler 412 provides an analog value indicative of the pressure signal to an A/D converter 414 of the A/D processor 410 at the selected frequency. The sampler 412 can, for example, operate in a sample mode or DSP scan mode. The sampler can also perform anti-aliasing filtering (such as low pass filtering at a suitable frequency) before the analog data is converted into digital form. The A/D converter 414 can convert the analog values received from the sampler 412 to digital values and store the digital values in an output buffer 416 of the A/D processor 410.

A filter 420 can access the digital values stored in the output buffer 416 and perform a filtering operation on the digital values. For example, the filter 420 can be an infinite impulse response (IIR) filter (or a finite impulse response (FIR) filter) and perform a low-pass filter (LPF) operation on the digital values to reduce higher frequency noise or smooth out rapid changes in the sampled pressure signal that are due to the pressure transients. The filter 420 thus can, for instance, maintain a continuous running average of the digital values over one or more cycles or a fraction of a cycle of opening and/or closing of one or more valves or rotation of a motor of the pump, such as the pump 390. In one example implementation, the filter operation performed by the filter 420 can be based on the following equation:

$$\text{filteredSample} = [\text{averager} = ([(\text{averager} - (\text{averager} >> \text{iirBitShift})) + \text{rawSample}] >> \text{iirBitShift})]$$

where rawSample can be a digital value removed from the output buffer 416, iirBitShift can be a constant weighting factor, averager can be a variable used to hold intermediate filter results, and filteredSample can be the output value of the filter 420. The filter 420 can store the filtered digital values from the filtering operation in the filter buffer 430. The filter 420 can, for instance, operate at the same frequency as the sampler 412 so that the filter 420 provides a filtered value for each digital value to the filter buffer 430 at the same frequency.

A storage processor 440 can access the filtered values stored in the filter buffer 430 and transfer the filtered values to a measures buffer 450 (e.g., a ring buffer) for further processing by the pump control processor (e.g., for additional averaging, to determine an estimated pressure near the inlet of the pump assembly, or to determine whether to trigger an alarm). In some embodiments, the storage processor 440 can sample the filtered values stored in the filter buffer 430 and transfer the sampled values to the measures buffer 450. As a result, the storage processor 440 may not, in some instances, access all of the filtered values stored in the filter buffer 430, but may access a selected subset of the filtered values for further processing. In one example, the storage processor 440 can access the filtered values and transfer the sampled values synchronous with the operation of the pump, such as after opening and/or closing of one or more valves of the pump. Advantageously, in certain embodiments, by sampling and transferring the filtered values synchronous with the operation of the pump, the storage processor 440 can avoid further processing of filtered values corresponding to a pressure transient created in the flow path on each opening and/or closing of one or more valves of the pump.

The filtered values corresponding to the pressure transient may contain more noise than other filtered values and thus may be less desirable for use in further processing by the pump control processor. In some embodiments, the storage processor 440 can sample the filtered values and transfer the sampled values to the measures buffer 450 in accordance with a timer (e.g., periodically, such as every 2 ms) and asynchronous with the operation of the pump when an operational speed of the pump falls below a threshold (e.g., a rotation speed of the pump falls below 1 Hz or 2 Hz) or the pump has been idle for at least a threshold period of time (e.g., 100 ms or 500 ms). That is, when the pump is operating slowly (for example, when activity of the pump falls below an activity threshold), asynchronous sampling can be utilized. The storage processor 440 can further transfer a system voltage and motor current of the pump (and/or any other measurement of the operation of the negative pressure apparatus) from the filter buffer 430 to the measures buffer 450.

The pump can include a tachometer or any other suitable device (as described) below for measuring rotation of the pump motor. For example, the pump can be a diaphragm pump operated by a DC motor and having inlet and outlet valves. One cycle of the pump can correspond to four rotations of the motor (or any other suitable number of rotations), and the tachometer can provide an indication for each rotation of the motor. Pressure sensor reading can be sampled by the sampler 412 and converted to digital data by the A/D converter at a frequency or rate that exceeds the rate of frequency at which the pump is operating (for example, as measured by the tachometer). The pressure is sampled at a higher frequency (or oversampled) as compared to the speed of the pump motor (as measured by the tachometer) and the opening and/or closing of either or both the inlet and outlet valves. Oversampling allows for removal (for example, by the filter 420) of contributions due to the pressure transients caused by the opening and/or closing of the valves. The filtered pressure values can be removed from the filter buffer 430 synchronous with (for example, upon arrival or detection of) the indication from the tachometer that the pump motor has turned. This achieves synchronous sampling.

In certain embodiments, synchronous sampling can be performed by directly identifying the time durations when the at least one pump valve opens and/or closes. For example, the pump, such as the pump 390, may utilize one or more sensors that sense opening and/or closing of the at least one valve. Information provided by the one or more sensors can be used to perform synchronous sampling. For instance, the pressure can be sampled sometime after the opening and/or closing of the valve as indicated by the one or more sensors. This time can be determine based on one or more threshold intervals, such as for instance 100 ms (or any other suitable time) after opening of the at least one valve.

In some embodiments, a pump assembly, such as pump assembly 230, controls the vacuum pump to deliver negative pressure therapy to a wound according to a selected or programmed protocol. Pump control can be performed by the pump control processor 370 alone or in combination with the processor 310. For example, as explained above, the user can select continuous operation at a desired pressure (or negative pressure setpoint). The pump assembly can activate the vacuum pump to reduce or draw down the pressure at the wound (e.g., under the dressing) to reach the setpoint. As explained below, the draw down can be performed by increasing the negative pressure at the wound limited by a maximum change in negative pressure per unit time called compression, until the setpoint has been achieved. Wound draw down can be defined as the period of time immediately after therapy has been initiated during which the wound has not yet achieved the setpoint. As explained below, at the end of this period when the setpoint is achieved, the flow rate in the fluid flow path should be below a leak (or high flow) threshold and above a low vacuum threshold, otherwise an appropriate alarm will be activated.

Figure 5:
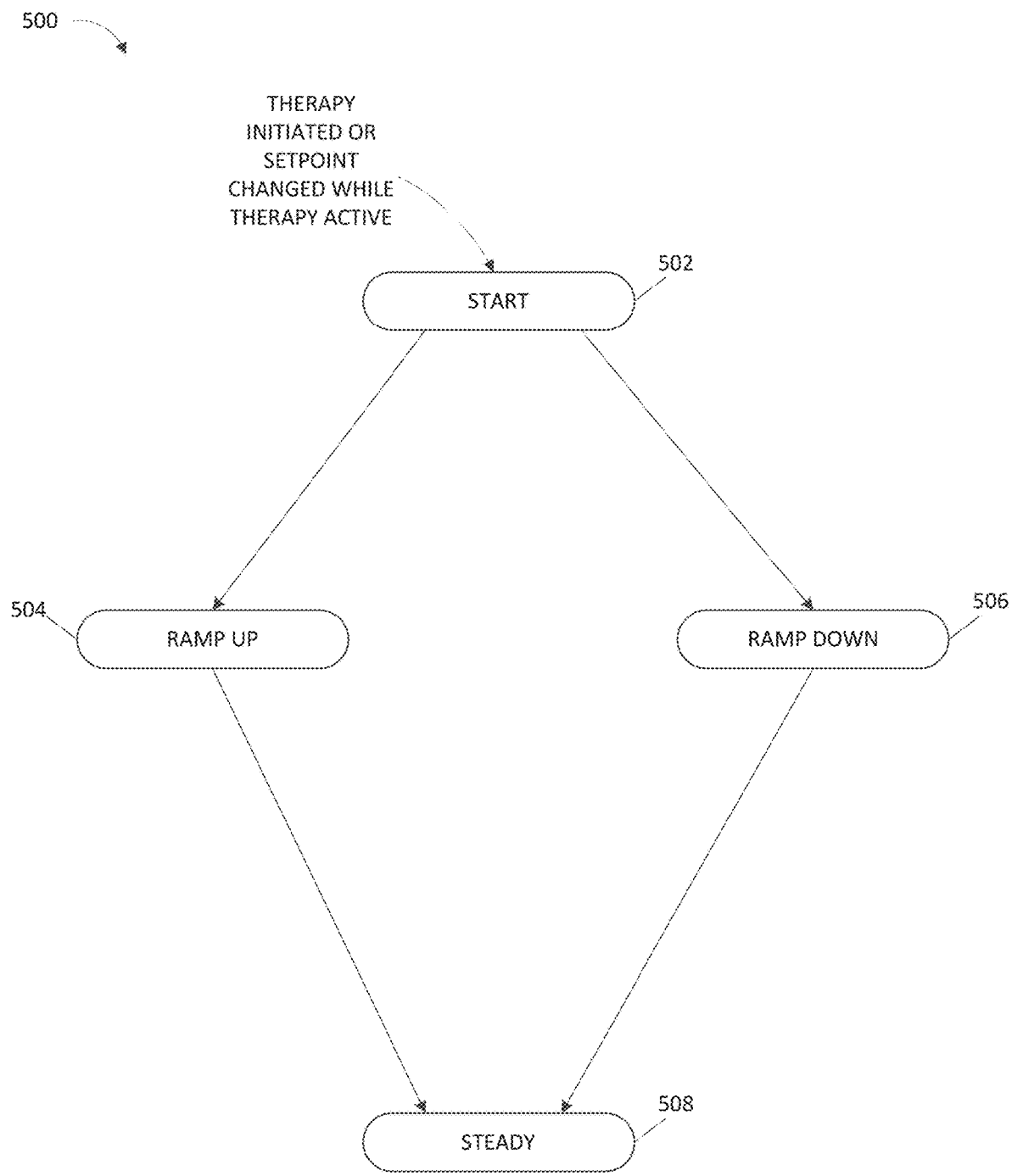
FIG. 5 illustrates a process of providing negative pressure wound therapy according to some embodiments.

FIG. 5 illustrates a process 500 for providing negative pressure wound therapy according to some embodiments. The process 500 can be executed by the pump control processor 370 alone or in combination with the processor 310. The process 500 can be periodically executed, such as for example every 100 milliseconds (or 10 times per second) or at any other suitable frequency. Alternatively or additionally, the process 500 can be continuously executed.

The process 500 can begin in block 502, which it can transition to when therapy is initiated or when the setpoint is changed while therapy is being delivered. In block 502, the process 500 compares wound pressure, which can be determined as explained below, to the setpoint. If the wound pressure is below the setpoint, the process 500 can transition to block 504. Conversely, if the wound pressure exceeds or is equal to the setpoint, the process 500 can transition to block 506.

In block 504 (pressure ramp up), the process 500 can increment a pump ramp setpoint by an amount that depends on the compression setting as explained below. The vacuum pump will then attempt to draw down the wound pressure to reach the current value of the pump ramp setpoint. For example, a suitable pump drive signal, such as voltage or current signal, can be generated and supplied to the pump motor so as to increase the speed of the pump motor to achieve wound draw down. For purposes of efficiency, the pump motor can be driven using PWM or any other suitable method. The process 500 can continue incrementing the pump ramp setpoint until it reaches the setpoint selected by the user. The process 500 can transition to block 508 when the wound pressure has nearly reached or reached the setpoint. For example, the process 500 can transition to block 508 when the wound pressure is within a ramp up threshold pressure of the setpoint, such as within 2 mmHg of the setpoint or within any other suitable value.

In block 506 (pressure ramp down), the process 500 can set the pump ramp setpoint to the setpoint selected by the user. The process 500 can deactivate the pump so that the wound pressure is allowed to decay, such as due to one or more leaks in the fluid flow path, to reach or almost reach the setpoint. At this point, the process 500 can transition to block 508. For example, the process 500 can transition to block 508 when the wound pressure is within a ramp down threshold pressure of the setpoint, such as within 5 mmHg of the setpoint or within any other suitable value. In some cases, the ramp down threshold pressure can be the same as the ramp up threshold pressure.

In block 508 (steady state), the pump ramp setpoint can be set to the setpoint selected by the user. The process 500 can control the vacuum pump to maintain the desired negative pressure at the wound. One or more conditions, such as high vacuum, low vacuum, leak, and the like can be detected in block 508 as is explained below. If the user changes the setpoint to be more negative or more positive or if delivery of therapy is paused, the process 500 can transition to block 502.

In some embodiments, the pump assembly controls the vacuum pump to draw down the wound (e.g., as is explained above in connection with block 504) by utilizing compression. Using compression can be beneficial for avoiding rapid changes in wound pressure, which can minimize patient discomfort, reduce noise produced as a result of operating the pump, maintain efficient delivery of negative pressure, maintain efficient use of power (e.g., battery power), and the like. Compression can be executed by the process 500, which in turn can be implemented by the pump control processor 370 alone or in combination with the processor 310. Compression can correspond to the maximum desired increase in negative pressure at the wound per unit of time. Compression can be determined based on the negative pressure setpoint and selected compression setting (e.g., low, medium, or high).

In some embodiments, the pump assembly monitors various parameters, such as pressure and rate of flow in the fluid flow path, in order to control the pump in connection with delivery of negative pressure wound therapy. Parameters monitoring and pump control can be performed by the pump control processor 370 alone or in combination with the processor 310. Monitoring the flow rate can be used, among other things, to ensure that therapy is properly delivered to the wound, to detect leakages, blockages, high pressure, and low vacuum, canister full, and the like.

The pump assembly can be configured to indirectly measure the flow rate in the fluid flow path. For example, the pump assembly can measure the speed (e.g., as frequency) of the vacuum pump motor by using a tachometer. Alternatively or additionally, the pump assembly can measure a level of activity or duty cycle of the pump using any suitable approach, such as by monitoring voltage or current supplied to the pump, sensing pump speed (e.g., by using a Hall sensor), measuring back EMF generated by the pump motor, monitoring duty cycle of the pump (for example, of the pump motor or actuator) and the like. Tachometer readings can be averaged (for example, by applying a low pass filter as explained above) in order to mitigate the effects of one or more errant readings. A number of most recent tachometer readings, such as over last 2.5 seconds or any other suitable time period, can be averaged to obtain short tachometer average. A number of less recent tachometer readings, such as over the last 30 seconds or any other suitable time period, can be averaged to obtain long tachometer average. Short and long tachometer averages can be utilized for pump control. Additionally or alternatively, the pump assembly can directly measure the flow rate, such as by using a flow meter.

In addition, the pump assembly can determine and monitor pressure in the flow path using one or more sensors. In some embodiments, the pump assembly includes a pressure sensor in or near the inlet 252 (or canister connection) of the pump assembly 230. This pressure sensor can measure the pressure in the canister or any other portion of the fluid flow path (or in or near the dressing or any other portion of the fluid flow path in a canisterless system). The arrangement of one or more pressure sensors in disclosed in U.S. patent application Ser. No. 14/210,062, filed on Mar. 13, 2014 and titled "SYSTEMS AND METHODS FOR APPLYING REDUCED PRESSURE THERAPY," which is incorporated by reference in its entirety. The pump assembly can continuously measure pressure in the canister, such as every millisecond or any other suitable duration. A suitable number of latest pressure sensor readings can be averaged to mitigate the effects of one or more errant readings.

Wound pressure can be estimated using the measured canister pressure and the pump speed. Because of presence of one or more leaks in the flow path, wound pressure may not be the same as canister pressure.

Based on the determined flow rate, canister pressure, and wound pressure values, the pump assembly monitor and detect various operating conditions and can control the pump. One or more of these conditions can be detected by the process 500 while the process in block 508. Blockage in the fluid flow path can be determined by comparing the flow rate, as reflected by long tachometer average, to a particular blockage threshold over or during a period of time, such as 2 minutes or any other suitable duration. The blockage threshold can be selected or determined based on the particular pressure setpoint. That is, to detect blockage, the pump assembly can utilize a plurality of blockage thresholds corresponding to particular pressure setpoints. As explained above, the flow rate can be indirectly determined by detecting and monitoring the pump speed. Long tachometer average can be compared to the blockage threshold. Alternatively or additionally, short tachometer average or any other suitable measure of flow rate can be compared to the blockage threshold.

Figure 6:
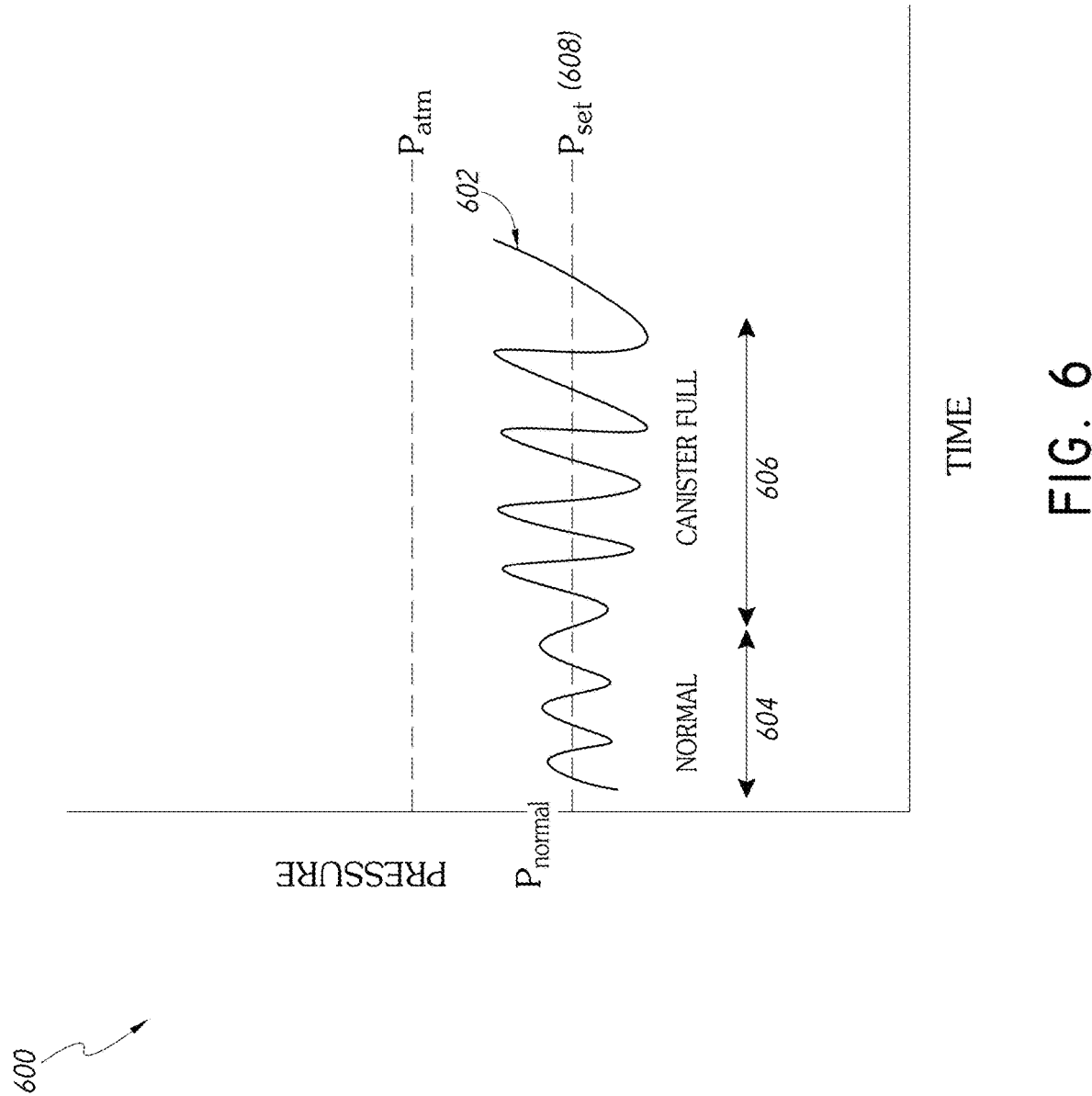
FIG. 6 illustrates pressure pulses according to some embodiments.

During operation, the pump generates pressure pulses (for example, pressure transients) that are propagated through the fluid flow path. The pressure pulses, which can be detected by a pressure sensor, are illustrated by the pressure curve 602 of FIG. 6 according to some embodiments. As is illustrated in region 604, pressure in the fluid flow path varies or oscillates around a particular pressure setpoint 608 during normal operation of the system. Region 606 illustrates pressure pulses in the flow path in presence of a blockage distal to the pump. For example, the canister (or dressing) becomes full and/or a canister (or dressing) filter is occluded or blocked. As is illustrated in region 606, presence of a distal blockage causes a reduced volume to be seen upstream of the canister (or dressing), and the amplitude of the pressure pulses changes (e.g., increases). The frequency of a pressure signal also changes (e.g., slows down or decreases). Observed changes in one or more parameters of the pressure signal can be used to identify the type of distal blockage present, such as distinguish between canister (or dressing) full and other types of blockages in the fluid flow path. Changes in the amplitude of the pressure signal can be measured using a variety of techniques, such as by measuring peak-to-trough change.

Figure 7:
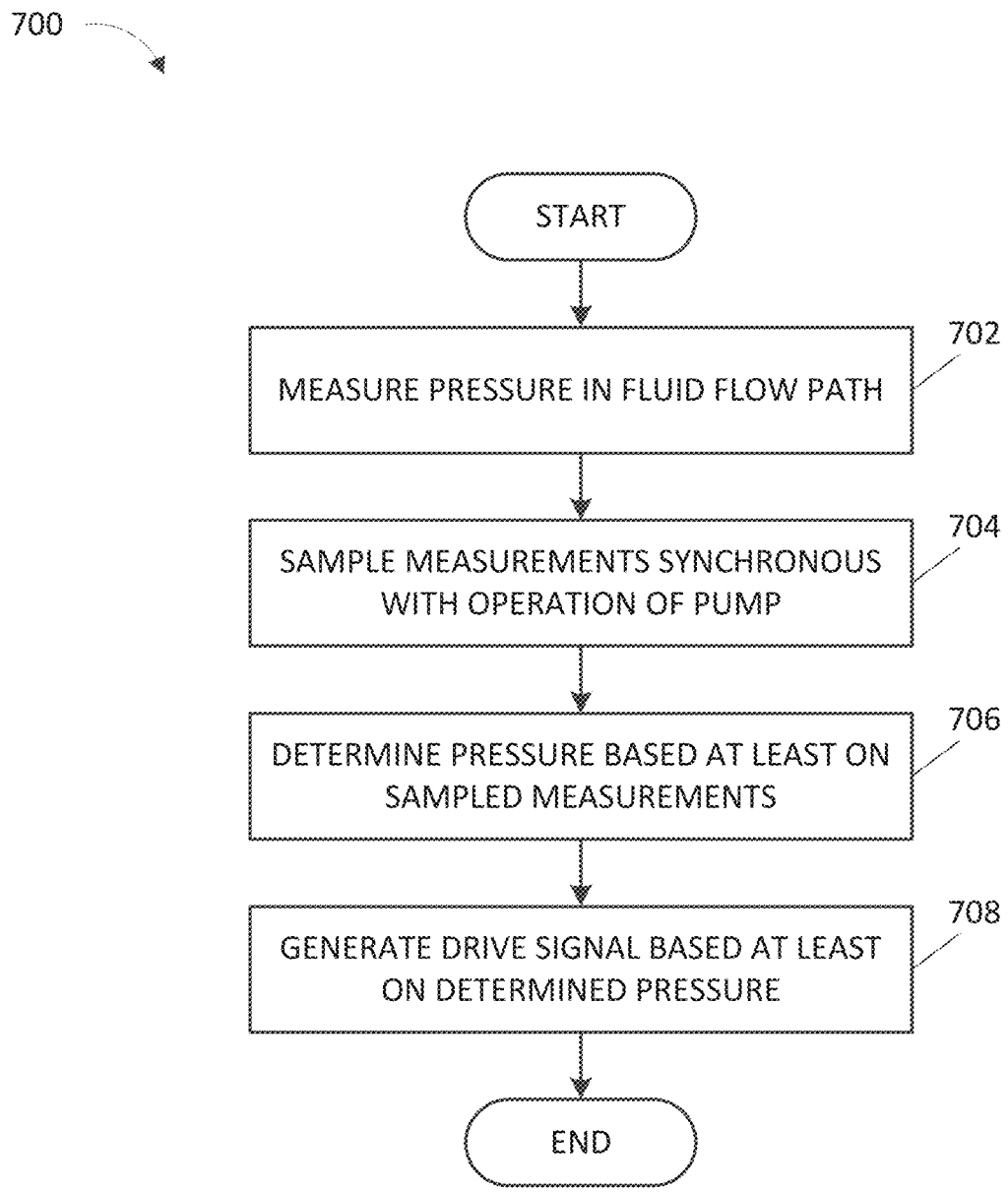
FIG. 7 illustrates a process of providing negative pressure wound therapy according to some embodiments.

FIG. 7 illustrates a process 700 of providing negative pressure wound therapy according to some embodiments. The process 700 can be executed by the pump control processor 370 alone or in combination with the processor 310. The process 700 can be periodically executed or at any other suitable frequency. Alternatively or additionally, the process 700 can be continuously executed. Advantageously, in certain embodiments, the process 700 can enable the synchronization of pressure measurements with the operation of a pump, such that the impact of pressure measurements corresponding to pressure transients created in the flow path due to the opening and/or closing of one or more valves of the pump can be reduced or eliminated.

At block 702, the process 700 can read measurements of pressure in a fluid flow path. The measurements may have been received from a pressure sensor positioned to sense the pressure at or near an inlet of a pump assembly, such as the pump assembly 230, or at any other suitable portion of the fluid flow path. In one example, the measurements may be obtained from the output buffer 416 may have further been filtered, such as by the filter 420, before being stored in the filter buffer 430.

At block 704, the process 700 can sample the identified measurements synchronous with opening and/or closing of one or more valves (e.g., an inlet valve or an outlet valve) of a pump, such as the pump 390, of the pump assembly. The measurements can thus be sampled such that one or more of the identified measurements are excluded from the sampled measurements. For instance, the measurements can be influenced by a pressure transient created by the periodic opening and/or closing of one or more valves of the pump, and the process 700 can sample the measurements so that one or more measurements more influenced by the pressure transient than are other of the measurements are excluded from the sampled measurements. The process 700 can, in some embodiments, determine the opening and/or closing of the one or more valves using a signal from the pump or a sensor associated with the pump.

In one example, the process 700 can sample the measurements at a sample frequency corresponding to (e.g., proportional to) a opening and/or closing frequency of one or more valves of the pump. In another example, the process 700 can sample the measurements so that the measurements measured when one or more valves of the pump is at one position in a opening and/or closing cycle are included in the sample measurements and the measurements measured when the one or more valves is at another position in the opening and/or closing cycle are excluded from the sample measurements.

In a further example, the process 700 can sample the measurements based at least on a rate or frequency of a signal received from a tachometer associated with the pump. The tachometer can be positioned to measure a speed of a motor of the pump. The sampling of the measurements can involve accessing and transferring pressure measurements for further processing, for instance, in response to detecting one or either of the rising edge and falling edge of the tachometer signal, such that of the sampling is synchronized with the rotation of the motor (or operation of the pump).

At block 706, the process 700 can determine pressure in the fluid flow path based at least on the sampled measurements. The pressure can, for instance, be determined such that one or more of the measurements that reflect contributions due to the pressure transients are excluded from the sampled measurements. The pressure can be more accurate than if the pressure were estimated based on both the sampled measurements and the measurements excluded from the sampled measurements, because the impact of a pressure transient created on each opening and/or closing of one or more valves of the pump can be reduced or eliminated by not considering the measurements excluded from the sampled measurements in the determination of the pressure.

At block 708, the process 700 can generate a drive signal based at least on the estimated pressure to control the operation of the pump. For example, the drive signal can be a PWM signal, and the duty cycle of the drive signal can be varied to increase or decrease the speed of the pump according at least to the estimated pressure. In some embodiments, the duty cycle of the drive signal can be controlled using a proportional-integral-derivative (PID) calculation based at least on a difference between a pressure setpoint and the estimated pressure as described with respect to process 800 of FIG. 8.

Although the process 700 is described as using sampling to reduce or eliminate the impact of pressure transients created by one or more valves of a pump, one or more additional or other approaches can be used in some embodiments to reduce or eliminate the impact of the pressure transients created by the one or more valves of the pump. For example, the process 700 can weight the measurements based at least on a synchronization of the measurements with opening and/or closing of the one or more valves of the pump. The measurements more influenced by a pressure transient created by the opening and/or closing of the one or more valves of the pump than other measurements can be given a reduced weighting relative to the other measurements so that the measurements more influenced by the pressure transient can influence the determined estimated pressure less than the other measurements.

Figure 8:
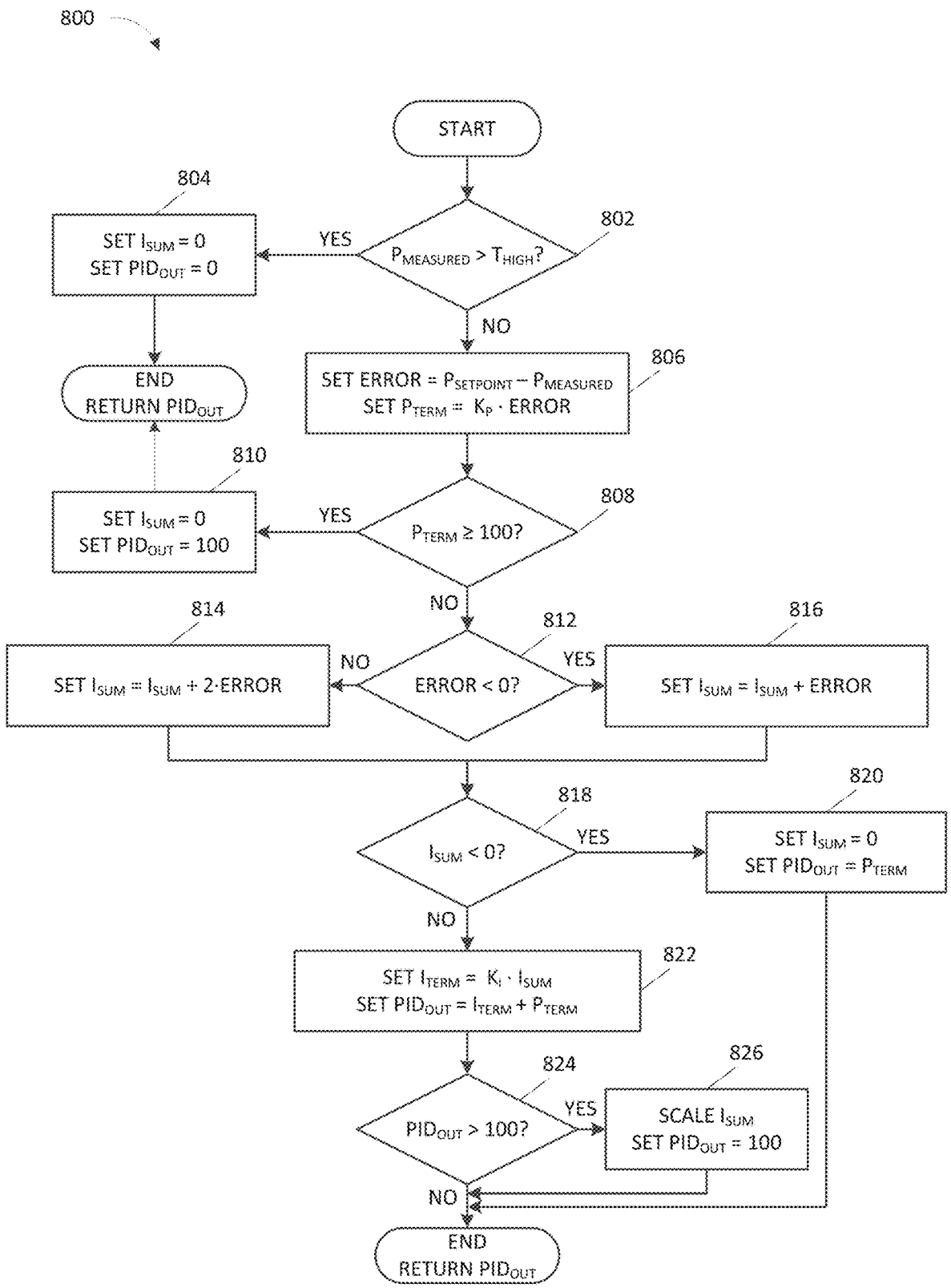
FIG. 8 illustrates a process for determining a duty cycle for a control signal for a source of negative pressure according to some embodiments.

FIG. 8 illustrates a process 800 for determining a duty cycle for a PWM control signal for a source of negative pressure according to some embodiments. The process 800 can be executed by the pump control processor 370 alone or in combination with the processor 310. The process 800 can be periodically executed or at any other suitable frequency. Advantageously, in certain embodiments, the process 800 can enable the pump control processor 370 to determine a suitable duty cycle for controlling a pump, such as the pump 390, so that the pump is ramped or controlled to a setpoint without (1) significantly overshooting the setpoint or (2) controlling the pump to operate at a level different from the setpoint under canister full conditions.

The process 800 can be based on a PID calculation and serve as a control loop feedback mechanism. The control loop feedback mechanism can provide up to three-term control according to an error value calculated based on a difference between a measured pressure and a setpoint pressure. The up to three-term control can be determined by a proportional control term ($P_{TERM}$), integral control term ($I_{TERM}$), or derivative control term ($D_{TERM}$). In some embodiments, the output of the PID calculation ($PID_{OUT}$) can depend on a sum of $P_{TERM}$, $I_{TERM}$, and $D_{TERM}$. The $I_{TERM}$, in addition, can be related to an integral sum ($I_{SUM}$) that can also depend on an accumulation of past errors. $PID_{OUT}$ can be set to permissibly range from 0 to 100 so that 0 corresponds to a 0% duty cycle PWM control signal and 100 corresponds to a 100% duty cycle PWM control signal. As illustrated by the process 800, in some embodiments, $D_{TERM}$ can be set to 0 during the process 800.

The process 800 can, in some ways, be similar to a standard PID calculation. However, the process 800 can include modifications to the standard PID calculation that improve the response of the PID calculation to various conditions in negative pressure wound therapy. For example, the process 800 can include the following modifications:

If a measured pressure exceeds a HighVacuumAlarmThreshold, $I_{SUM}$ can be set to 0.

If $P_{TERM}$ exceeds 100, $I_{SUM}$ can be set to 0 and $PID_{OUT}$ can be set to 100.

If a difference between a pressure setpoint and a measured pressure is negative, $I_{SUM}$ can be set to the sum of $I_{SUM}$ and a value greater than the difference.

If $I_{SUM}$ is less than 0, $I_{SUM}$ can be set to 0 and $PID_{OUT}$ can be set to $P_{TERM}$, which can prevent long PID restart delays following periods of pressure release.

If a sum of $P_{TERM}$ and $I_{TERM}$ exceeds 100, $PID_{OUT}$ can be set to 100 and $I_{SUM}$ can be reduced, such as proportional to an amount that the sum exceeds 100.

Although the process 800 may include all of the above-referenced modifications, in some embodiments, the process 800 can instead include one or more of the modifications and not one or more other of the modifications, or may include different modifications.

At block 802, the process 800 can determine whether a measured pressure ($P_{MEASURED}$) in the flow path exceeds a high vacuum threshold ($T_{HIGH}$). The measured pressure can be a pressure measurement received from a pressure sensor positioned at or near an inlet of a pump assembly, such as the pump assembly 230, and, in some embodiments, may have been sampled from a set of measurements as discussed with respect to process 700. If the measured pressure exceeds the high vacuum threshold, at block 804, the process 800 can set $I_{SUM}$ to be 0 and $PID_{OUT}$ to be 0, and the process 800 can end by returning the value of $PID_{OUT}$.

If the measured pressure does not exceed the high vacuum threshold, at block 806, the process 800 can set ERROR to be a difference between a pressure setpoint and the measured pressure and set $P_{TERM}$ to be a proportional gain ($K_P$) times ERROR. The pressure setpoint can be set, for example, by a user of a pump assembly by setting a desired pressure or a mode of operation that corresponds to the pressure setpoint. In some embodiments, the proportional gain can be set at pump assembly manufacture or during a test operation of a pump assembly using one or more control loop tuning approaches. The proportional gain can, for instance, be set to a value ranging from 0 to 1, ranging from 0.3 to 0.9, ranging from 0.5 to 0.7, or 0.6.

At block 808, the process 800 can determine whether $P_{TERM}$ equals or exceeds 100. If $P_{TERM}$ equals or exceeds 100, at block 810, the process 800 can set $I_{SUM}$ to be 0 and $PID_{OUT}$ to be 100, and the process 800 can end by returning the value of $PID_{OUT}$. If $P_{TERM}$ does not equal or exceed 100, at block 812, the process 800 can determine whether ERROR is below 0. If ERROR is not below 0, the process 800 can set $I_{SUM}$ to be a sum of $I_{SUM}$ and 2 times ERROR at block 814. If ERROR is below 0, the process 800 can set $I_{SUM}$ to be a sum of $I_{SUM}$ and ERROR at block 816. At block 818, the process 800 can determine whether $I_{SUM}$ is less than 0. If $I_{SUM}$ is less than 0, at block 820, the process 800 can set $I_{SUM}$ to be 0 and $PID_{OUT}$ to be $P_{TERM}$, and the process 800 can end by returning the value of $PID_{OUT}$.

If $I_{SUM}$ is not less than 0, at block 822, the process 800 can set $I_{TERM}$ to be an integral gain ($K_1$) times $I_{SUM}$ and set $PID_{OUT}$ to be a sum of $P_{TERM}$ and $I_{TERM}$. In some embodiments, the proportional gain can be set to a value ranging from 0 to 1, ranging from 0.0001 to 0.0003, or to 0.0002. At block 824, the process 800 can determine whether $PID_{OUT}$ exceeds 100. If $PID_{OUT}$ does not exceed 100, process 800 can end by returning the value of $PID_{OUT}$. If $PID_{OUT}$ exceeds 100, at block 826, the process 800 can scale $I_{SUM}$ (e.g., by an amount depending on or proportional to the amount that $PID_{OUT}$ exceeds 100) and set $PID_{OUT}$ to be 100, and the process 800 can end by returning the value of $PID_{OUT}$.

Figure 9A:
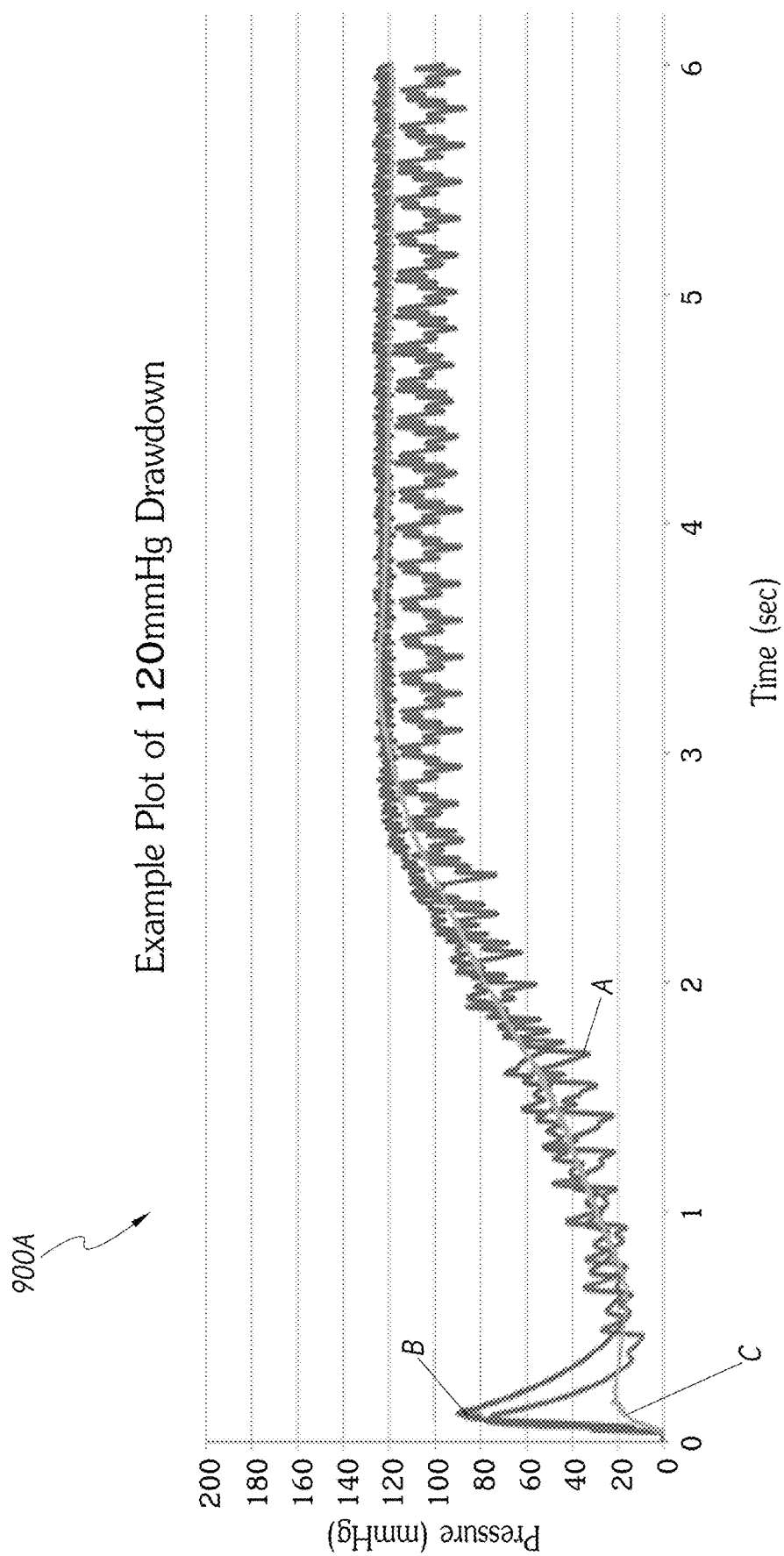
FIGS. 9A-9B and 10A-10B illustrate plots of operating pressure for simulated reduced pressure wound therapy systems according to some embodiments.
Figure 9B:
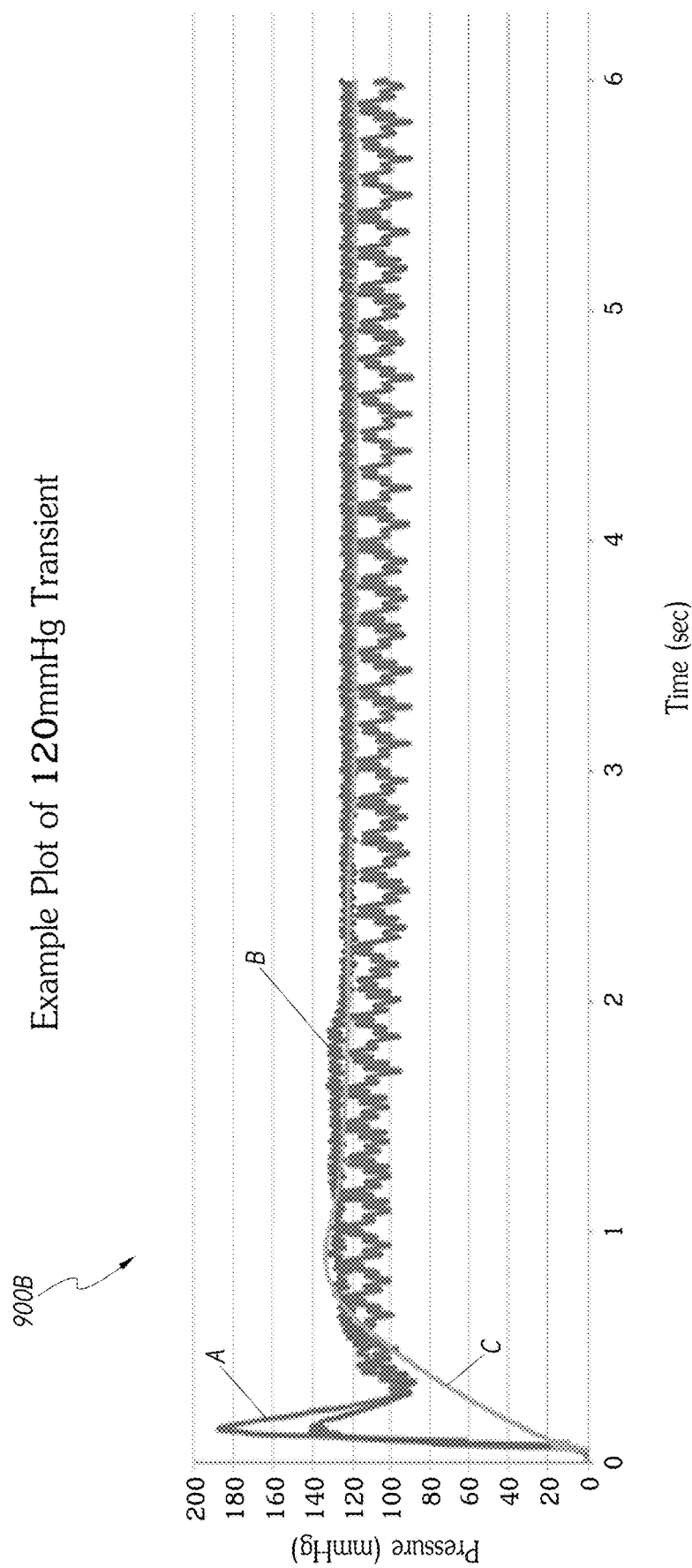
Figure 10A:
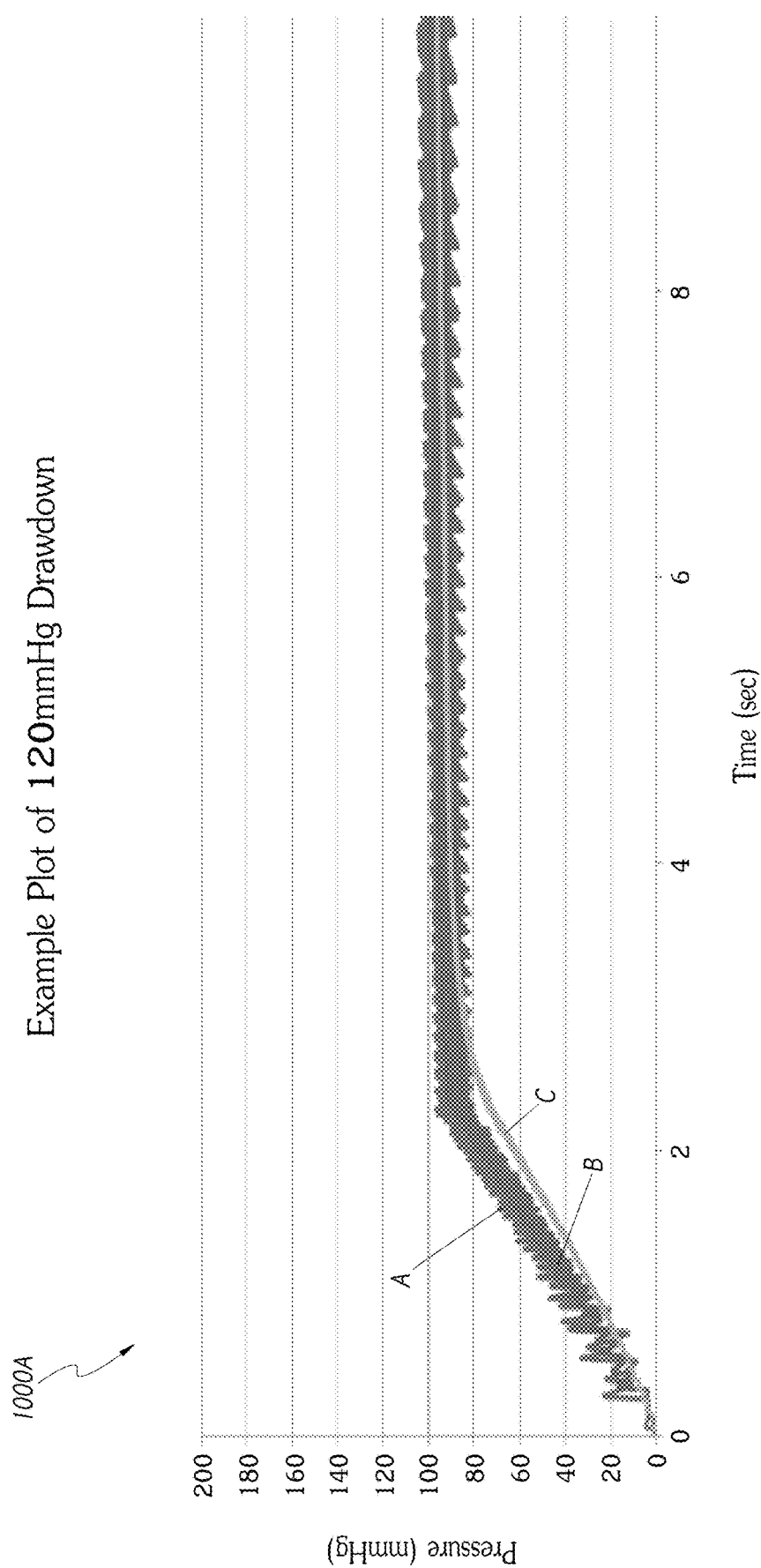
Figure 10B:
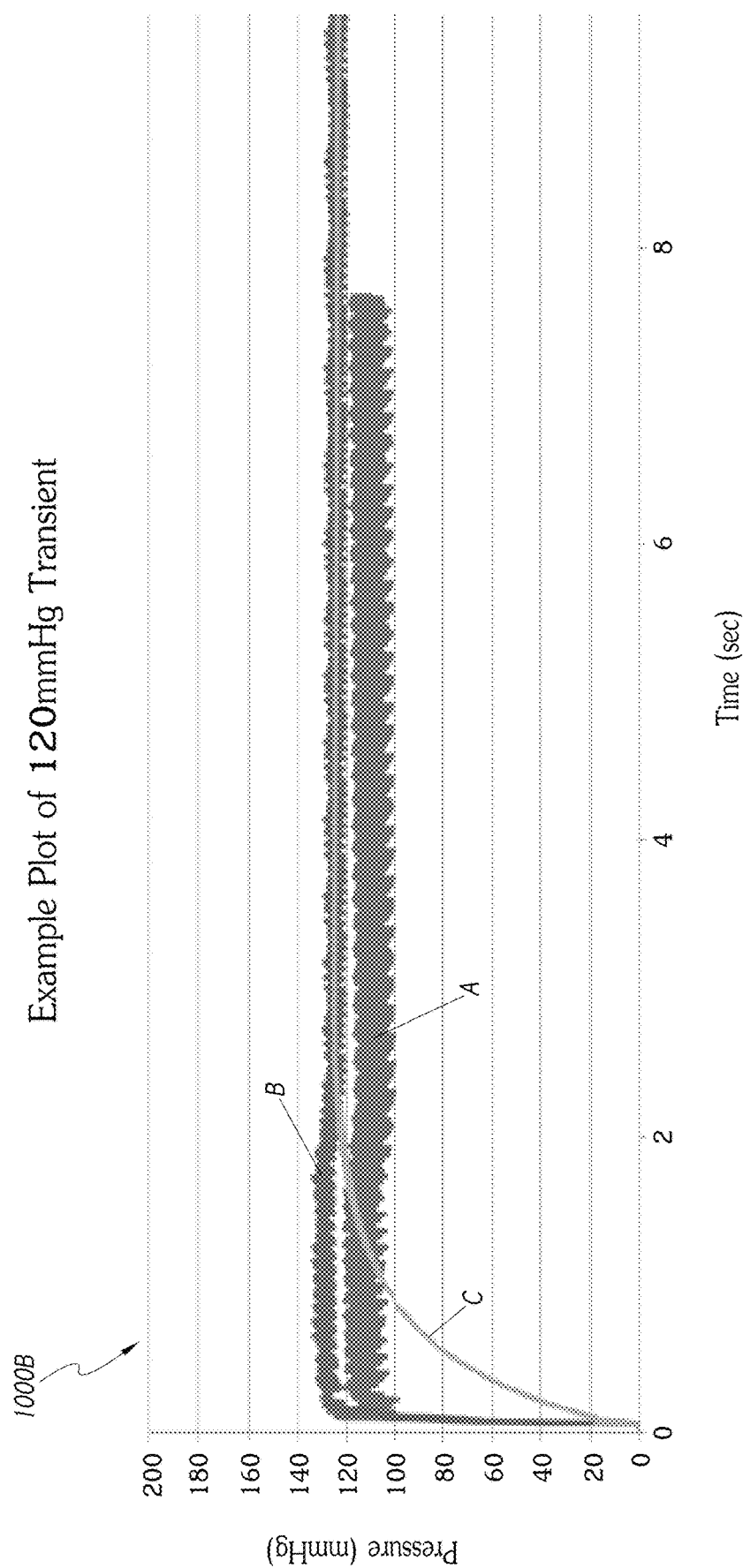

FIGS. 9A-9B and 10A-10B illustrate plots of operating pressure for simulated reduced pressure wound therapy systems according to some embodiments. FIGS. 9A-9B depict example plots of operating pressure for a simulated system that does not implement at least some of the teachings provided in this disclosure, such as the teachings described with respect to the process 700 (e.g., using sampled pressure values) and the process 800 (e.g., PID calculation based control process). FIGS. 10A-10B depict example plots of operating pressure for a simulated system that does implement at least some of the teachings provided in this disclosure, such as the teachings described with respect to the processes 700 and 800.

FIG. 9A shows an example plot 900A for a draw down operation and controlling of a pump to attempt to draw down a pressure at the wound to reach 120 mmHg without using synchronous sampling. The lines A, B, and C of the plot 900A respectively illustrate the simulated operating pressure for the system with a full canister, nearly full canister, and empty canister. At a time of 0 seconds, the pump begins operating so as to draw down the pressure. At around a time of 3 seconds, the pump has finished the draw down and entered steady-operation. As can be seen from the lines A and B of the plot 900A, the pressure in the simulated systems indicates presence of a significant pressure pulse or transient between 0 seconds to 0.5 seconds (which is not removed because synchronous sampling is not used). Operating the pump without removing or mitigating contributions due to such a pressure pulse or transient at the startup of the pump may not be desirable in some instances and, for example, may be uncomfortable or painful for a patient. In addition, it can be seen from line A of plot 900A that the canister full condition may also cause the pump to draw down by 100 mmHg rather than 120 mmHg as desired. Thus, the pump may also be underperforming under canister full conditions (or even under canister empty or relatively empty conditions).

FIG. 9B shows an example plot 900B for controlling of a pump in a presence of a pressure transient of 120 mmHg without using synchronous sampling. The lines A, B, and C of the plot 900B respectively illustrate the simulated operating pressure for the system with a full canister, nearly full canister, and empty canister. At a time of 0 seconds, the pump begins operating to draw down the pressure at the wound. The time between 0 and 1 second illustrates occurrence of a pressure transient (which is not removed because synchronous sampling is not used). At around a time of 1 second, the pressure transient has ceased or ended. As can be seen from the lines A and B of the plot 900B, the pressure in the simulated systems can show a significant pressure overshoot between 0 seconds to 0.3 seconds as a result of the pressure transient. Operating the pump without removing or mitigating contributions due to such a pressure overshoot may not be desirable in some instances and, for example, may be uncomfortable or painful for a patient. In addition, it can be seen from line A of plot 900B that the canister full condition may cause the pump to adjust pressure by 100 mmHg rather than 120 mmHg as desired. Thus, the pump can be underperforming under canister full conditions (or even under canister empty or relatively empty conditions).

FIG. 10A shows an example plot 1000A for a draw down operation and controlling of a pump to attempt to draw down a pressure by 120 mmHg, and FIG. 10B shows an example plot 1000B for a transient operation and controlling of a pump in the context of a pressure transient of 120 mmHg. In both plots 1000A and 1000B synchronous sampling is utilized. In contrast to FIGS. 9A-9B, as can be seen from the lines A, B, and C of the plots 1000A and 1000B, FIGS. 10A-10B show a smooth draw down in pressure, minimal overshoot after a transient event, relatively fast adjustment to reach a pressure setpoint, and effective adjustment of pressure independent of a remaining capacity of a canister. Moreover, as can be seen from the line A of the plots 1000A and 1000B, the pressure can be adjusted closer to a pressure setpoint than may have been achievable in the systems depicted by the plots 900A and 900B. Accordingly, use of synchronous sampling for controlling the pump results, for example, in increased efficiency, diminished noise and vibration caused by operation of the pump, reduced in energy usage, and better comfort for the patient.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. An apparatus for applying negative pressure therapy to a wound, the apparatus comprising:
   a source of negative pressure configured to be fluidically connected via a fluid flow path with a wound covered by a wound dressing;
   a pressure sensor configured to monitor pressure in the fluid flow path; and
   a controller in communication with the pressure sensor, the controller being configured to:
      determine a first pressure in the fluid flow path from the pressure sensor without synchronizing determination of pressure in the fluid flow path with at least one of opening or closing of at least one of an inlet valve or an outlet valve of the source of negative pressure responsive to an activity level of the source of negative pressure being below a first activity threshold associated with the source of negative pressure being active and being above a second activity threshold associated with the source of negative pressure being inactive, and
      operate the source of negative pressure using the first pressure in the fluid flow path.

2. The apparatus of claim 1, wherein the controller is configured to activate the source of negative pressure responsive to the first pressure in the fluid flow path not satisfying a negative pressure threshold.

3. The apparatus of claim 2, wherein controller is configured to deactivate the source of negative pressure responsive to the first pressure in the fluid flow path satisfying the negative pressure threshold.

4. The apparatus of claim 3, wherein subsequent to the first pressure in the fluid flow path satisfying the negative pressure threshold, the controller is configured to operate the source of negative pressure to maintain pressure in the fluid flow path at a negative pressure level corresponding to the negative pressure threshold.

5. The apparatus of claim 1, further comprising at least one indicator configured to indicate operational status of the apparatus, wherein the controller is configured to activate and deactivate the at least one indicator.

6. The apparatus of claim 5, wherein the at least one indicator comprises first and second indicators configured to emit different colors of light.

7. The apparatus of claim 6, wherein the first indicator is configured to emit a green color of light, and wherein the controller is configured to activate the first indicator to indicate normal operational status and activate the second indicator to indicate abnormal operational status.

8. The apparatus of claim 1, wherein the controller is configured to:
   determine a duty cycle of the source of negative pressure, and
   determine presence of a leak in the fluid flow path responsive to a determination that the duty cycle satisfies a leak threshold.

9. The apparatus of claim 8, further comprising an indicator, wherein the controller is configured to activate the indicator responsive to a determination that the leak is present in the fluid flow path.

10. A negative pressure wound therapy system comprising the apparatus of claim 9 and the wound dressing.

11. The apparatus of claim 1, wherein the controller is further configured to:
   determine a second pressure in the fluid flow path from the pressure sensor by synchronizing determination of pressure in the fluid flow path with at least one of opening or closing of at least one of the inlet valve or the outlet valve of the source of negative pressure responsive to the activity level of the source of negative pressure being above the first activity threshold; and
   operate the source of negative pressure using the second pressure in the fluid flow path.

12. An apparatus for applying negative pressure therapy to a wound, the apparatus comprising:
   a source of negative pressure configured to be fluidically connected via a fluid flow path with a wound covered by a wound dressing;
   a pressure sensor configured to measure a pressure in the fluid flow path; and
   a controller in communication with the pressure sensor, the controller being configured to:
      determine a first pressure in the fluid flow path from a first plurality of measurements received from the pressure sensor, the first plurality of measurements having been measured by the pressure sensor without synchronizing determination of pressure in the fluid flow path with at least one of opening or closing of at least one of an inlet valve or an outlet valve of the source of negative pressure responsive to an activity level of the source of negative pressure being below a first activity threshold associated with the source of negative pressure being active and being above a second activity threshold associated with the source of negative pressure being inactive; and activate or deactivate the source of negative pressure according to the first pressure in the fluid flow path.

13. The apparatus of claim 12, wherein the controller is configured to activate the source of negative pressure responsive to the first pressure in the fluid flow path not satisfying a negative pressure threshold.

14. The apparatus of claim 13, wherein controller is configured to deactivate the source of negative pressure responsive to the first pressure in the fluid flow path satisfying the negative pressure threshold.

15. The apparatus of claim 14, wherein subsequent to the first pressure in the fluid flow path satisfying the negative pressure threshold, the controller is configured to operate the source of negative pressure to maintain pressure in the fluid flow path at a negative pressure level corresponding to the negative pressure threshold.

16. The apparatus of claim 12, further comprising at least one indicator configured to indicate operational status of the apparatus, wherein the controller is configured to activate and deactivate the at least one indicator.

17. The apparatus of claim 16, wherein the at least one indicator comprises first and second indicators configured to emit different colors of light.

18. The apparatus of claim 17, wherein the first indicator is configured to emit a green color of light, and wherein the controller is configured to activate the first indicator to indicate normal operational status and activate the second indicator to indicate abnormal operational status.

19. The apparatus of claim 12, wherein the controller is configured to:

determine a duty cycle of the source of negative pressure, and determine presence of a leak in the fluid flow path responsive to a determination that the duty cycle satisfies a leak threshold.

20. The apparatus of claim 19, further comprising an indicator, wherein the controller is configured to activate the indicator responsive to a determination that the leak is present in the fluid flow path.

21. A negative pressure wound therapy system comprising the apparatus of claim 12 and the wound dressing.

22. The apparatus of claim 12, wherein the controller is further configured to:

determine a second pressure in the fluid flow path from a second plurality of measurements received from the pressure sensor, the second plurality of measurements having been measured by the pressure sensor by synchronizing determination of pressure in the fluid flow path with at least one of opening or closing of at least one of the inlet valve or the outlet valve of the source of negative pressure responsive to the activity level of the source of negative pressure being above the first activity threshold; and activate or deactivate the source of negative pressure according to the second pressure in the fluid flow path.

* * * * *